(12) United States Patent
Pasternack et al.

(10) Patent No.: US 7,062,962 B2
(45) Date of Patent: Jun. 20, 2006

(54) PORTABLE APPARATUS AND METHOD FOR MEASURING HYDRAULIC FEATURES IN RIVERS AND STREAMS

(75) Inventors: Greg Pasternack, Davis, CA (US); Brett Valle, San Francisco, CA (US); David Paige, Woodland, CA (US); Ken M. Shaw, Vacaville, CA (US)

(73) Assignee: The Regents of the University of California, Oakland, CA (US)

( * ) Notice: Subject to any disclaimer, the term of this patent is extended or adjusted under 35 U.S.C. 154(b) by 93 days.

(21) Appl. No.: 10/821,410

(22) Filed: Apr. 9, 2004

(65) Prior Publication Data

US 2005/0223792 A1    Oct. 13, 2005

(51) Int. Cl.
*G01C 5/00* (2006.01)
(52) U.S. Cl. .................................. 73/170.29
(58) Field of Classification Search ............. 73/170.29, 73/866.5; 212/223, 225
See application file for complete search history.

(56) References Cited

U.S. PATENT DOCUMENTS

| | | | | |
|---|---|---|---|---|
| 2,180,354 A | * | 11/1939 | Frazier | 73/170.33 |
| 2,200,274 A | * | 5/1940 | Hayes | 212/296 |
| 2,631,453 A | * | 3/1953 | Larsen et al. | 73/147 |
| 2,684,109 A | * | 7/1954 | Youmans | 472/13 |
| 2,896,908 A | * | 7/1959 | Stone | 254/1 |
| 3,215,436 A | * | 11/1965 | Carter | 473/171 |
| 3,314,009 A | * | 4/1967 | Murdock | 340/870.38 |
| 3,534,605 A | * | 10/1970 | Koning et al. | 73/290 R |
| 3,780,578 A | * | 12/1973 | Sellman et al. | 73/227 |
| 3,796,322 A | * | 3/1974 | Cording | 212/282 |
| 4,854,166 A | * | 8/1989 | Futrell, II | 73/170.29 |
| 4,866,985 A | * | 9/1989 | Futrell, II | 73/170.29 |
| 5,439,800 A | * | 8/1995 | Thompson | 435/9 |
| 5,734,111 A | * | 3/1998 | Hak Soo | 73/861.25 |
| 5,907,111 A | * | 5/1999 | Josten et al. | 73/866.5 |
| 5,942,440 A | * | 8/1999 | Dooley et al. | 436/146 |
| 6,282,943 B1 | * | 9/2001 | Sanders et al. | 73/23.2 |
| 2003/0177851 A1 | * | 9/2003 | Henry et al. | 73/866.5 |
| 2004/0126205 A1 | * | 7/2004 | Amoss et al. | 414/138.5 |
| 2004/0177932 A1 | * | 9/2004 | Senesac et al. | 160/89 |

FOREIGN PATENT DOCUMENTS

| | | | | |
|---|---|---|---|---|
| JP | 60233562 A | * | 11/1985 |
| JP | 60263863 A | * | 12/1985 |
| JP | 61283823 A | * | 12/1986 |

* cited by examiner

*Primary Examiner*—Edward Lefkowitz
*Assistant Examiner*—George P Bonanto
(74) *Attorney, Agent, or Firm*—John P. O'Banion

(57) ABSTRACT

A portable apparatus for measuring characteristics of hydraulic features in rivers and streams that are unwadeable. The apparatus consists of a tripod base, a horizontal boom that articulates on the tripod, a carriage configured to travel on the boom, and a measuring rod that can be moved vertically on the carriage. These components are designed to be portable, carried by hand or in a raft, and are adapted to be assembled on rugged terrain. The measuring rod is configured to accommodate sensors to measure characteristics such as channel topography, water surface topography, air-water mixing, velocity pressure differentials, and lift and drag forces. The apparatus can be adapted for measurement and monitoring in harsh environments such as volcanic lakes, fumaroles, and hot springs. The invention can be utilized for sampling air quality, weather, water quality, fluid mechanics (gas or liquid), soils, sediments, volcanic gases and hydrothermal fluids.

29 Claims, 14 Drawing Sheets

PORTABLE APPARATUS AND METHOD FOR MEASURING HYDRAULIC FEATURES IN RIVERS AND STREAMS

CROSS-REFERENCE TO RELATED APPLICATIONS

Not Applicable

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to measurement of hydraulic features, and more particularly to measurement of the characteristics of hydraulic features in rivers and streams.

2. Description of Related Art

Water flows in rivers and streams are influenced by many hydraulic features including waterfalls, channel steps, knickpoints, weirs, spillways, dams and hydraulic jumps. Hydraulic jumps, for example, are turbulent mixtures of air and water that flow upward, such as downstream of a waterfall or as a roller in a swift moving river. Only two ingredients are needed for a jump to form-a flow obstruction and appropriate water discharge. Natural boulders, woody debris, alluvial bedforms, and abrupt channel geometry changes are examples of frequently occurring natural flow obstructions in channels. In addition, engineered structures such as weirs, check dams, and spillways can induce hydraulic jumps. Along with a flow obstruction, a hydraulic jump needs a specific water flow. If discharge is too low, water will flow around the obstruction. If discharge is too high, excessive water depth will drown the jump.

In this example of a hydraulic feature, naturally occurring hydraulic jumps, are very important because they induce rapid channel change by focusing energy in highly localized portions of the river. This results in oxygenation through their turbulent air-water mixing, habitat for some aquatic organisms, and a natural stressor for other aquatic organisms.

Scientists have a need to assess the internal structure and dynamics of naturally-occurring hydraulic features, and their role in geomorphic channel processes, sediment transport, basin evolution, water quality, and effect on the aquatic food web. Past research on hydraulic features has focused on the effect of dams and weirs and, to a small extent, their risk to unaware swimmers. Fluid mechanics of natural hydraulic features are an important factor in fluvial geomorphology, water quality, and aquatic ecology. For example, significant differences between idealized and natural hydraulic features constrain direct application of traditional fluid dynamics to engineered structures designed to duplicate natural hydraulic features. However, detailed measurements of the characteristics of a natural hydraulic feature can be used to formulate fluid mechanics equations to compute mass, momentum, and energy fluxes as well as provide multivariate statistical data to analyze and classify hydraulic features according to their hydrodynamic structure and function. With accurate measurements, formulated models can be applied to create complex dynamic flow models of natural hydraulic features and thereby construct and deploy effective hydraulic structures to incite channel change and revitalize altered and damaged riparian ecosystems.

The primary characteristics to measure in natural hydraulic features are channel topography, water surface topography, air-water mixing, velocity pressure differentials, and lift and drag forces. Measurement of these characteristics have been accomplished downstream of some dams and weirs where water releases are regulated and access from the dam structure, bridges or improved shorelines is easily obtained. However most natural hydraulic features, hydraulic jumps for example, are in inaccessible locations for vehicles or boats and are in highly unwadable rivers and streams. Rugged terrain around many mountain rivers necessitate portable equipment that can be carried by hand or in a raft. Additionally, uneven ground, deep pools, strong currents and turbulent conditions present in and around natural hydraulic features prevent safe wading, floating or swimming to collect measurements. Wading is typically constrained to velocities approaching 1.5 m/s and depths approaching 1.5 m. Cold water, algal biofilms, and poor subsurface visibility further constrain human stability in high velocity zones. As a result, attempted field investigations have been restricted to sites that are shallow, slow or accessible by a vehicle.

Portable measuring and monitoring equipment and methods to make accurate measurements of the characteristics of natural hydraulic features in rivers and streams are needed.

BRIEF SUMMARY OF THE INVENTION

The invention is a portable apparatus that can be carried over rugged terrain to a remote site and assembled to accurately measure characteristics of a hydraulic feature in an unwadeable river or stream. The apparatus uses a secure platform with a swing boom structure and a carriage to position a vertical measuring rod over the desired location of the hydraulic feature. Systematic measurements are taken of the bed and water surface topography as well as fluid mechanics in the study region at any desired specified point within the measurable region. For complete mapping from one reference point, one may systematically measure using a polar coordinate pattern.

Additionally, the apparatus can be adapted to measure or record events in streams and rivers such as variable dam outflows, flood pulses, changes in turbidity or for observing aquatic life movement and behavior. The invention can be used for measurement and monitoring in harsh environments such as volcanic lakes, fumaroles, and hot springs. The invention may also have application in industry for monitoring liquids or gases, and non water applications, such as measurement in a crevasse, are contemplated. The invention can be utilized for sampling air quality, weather, water quality, fluid mechanics (gas or liquid), soils, sediments, volcanic gases and hydrothermal fluids.

In one embodiment, a portable apparatus for measuring characteristics of a hydraulic feature in a river or stream comprises a measuring rod adapted to measure characteristics of a hydraulic feature, means for positioning the measuring rod in a desired location relative to a hydraulic feature, and a platform adapted to support the positioning means where the platform is adapted to be positioned adjacent the hydraulic feature.

In one embodiment, the measuring rod has a hollow hexagonal cross section. In another embodiment, the measuring rod has a round tubular cross section.

In one embodiment, the measuring rod has a visual index to measure the position of said measuring rod relative to said positioning means.

In one embodiment, the measuring rod is adapted to accommodate sensors selected from the group consisting essentially of a differential pressure sensor, a time domain reflectometer, a current meter, a propeller, an electromagnetic velocimeter, an acoustic Doppler velocimeter, a digital camera and a video camera.

In one embodiment, the platform comprises a tripod having adjustable legs. In another embodiment, the platform comprises a tripod having adjustable legs, a mast coupled to the tripod, and a support cable having a first end, a mid portion and a second end, wherein the first end of the support cable is coupled to the boom, the mid portion of the support cable is slidingly coupled to the mast; and the second end of the support cable is coupled to an anchoring object.

In one embodiment, the means for positioning comprises a boom oriented horizontally and coupled to the platform wherein the boom is adapted to articulate on a vertical axis through the platform and further adapted to extend over a hydraulic feature, and a carriage adapted to travel along the boom and further adapted to position said measuring rod vertically, wherein the measuring rod is positioned to measure a characteristic of a hydraulic feature when the boom is positioned at a desired orientation on the platform, the carriage is positioned at a desired location on said boom, and the measuring rod is positioned at a desired elevation relative to a hydraulic feature.

In another embodiment, the means for positioning further comprises a winch coupled to the boom, a winch cable having a first end and a second end, a pulley coupled to the carriage and adapted to support the winch cable, where the first end of the cable is coupled to the winch and the second end of the cable is coupled to the measuring rod, wherein the measuring rod is repositioned upward when the winch cable is retracted by the winch through the pulley.

In another embodiment, the means for positioning further comprises a support carriage adapted to travel on the boom, a support rod slidingly coupled to the support carriage and adapted to contact the ground and provide vertical support to the boom through the support carriage, wherein the boom is supported when the support carriage is positioned in a desired location on the boom and the support rod is positioned to contact the ground and is secured to the support carriage.

In one embodiment, the boom comprises a truss with at least two legs and the carriage is configured to travel on two legs of the truss.

An aspect of the invention is a portable apparatus for measuring the characteristics of a hydraulic feature consisting of a measuring rod, a portable platform, and a means for positioning the measuring rod in a hydraulic feature.

Another aspect of the invention is a portable apparatus that can be disassembled, carried by a person or in a raft, and assembled in the field.

A further aspect of the invention is an apparatus that can adapt to rugged terrain conditions adjacent to a hydraulic feature.

Another aspect of the invention is a measuring rod adapted to accommodate one or more sensors including a differential pressure sensor, a time domain reflectometer, a current meter such as a propeller, an electromagnetic velocimeter, and an acoustic Doppler velocimeter, a digital camera and a video camera.

A further aspect of the invention is a measuring rod with a hollow hexagonal cross section.

A still further aspect of the invention is a measuring rod with a round tubular cross section.

Another aspect of the invention is a measuring rod with a visual index to visually measure the positiori of the measuring rod.

Another aspect of the invention is a sectional measuring rod that can be adapted with additional sections for desired length.

A further aspect of the invention is a measuring rod with a taper section at the lower end for positioning over a fine point.

Another aspect of the invention is a measuring rod with a positioning device such as a transit prism, 360 degree prism or GPS at the top end.

A still further aspect of the invention is a portable apparatus for measuring a hydraulic feature consisting of a tripod with adjustable legs, a horizontal boom, a carriage that travels on the boom, and a measuring rod that is moved vertically on the carriage.

Another aspect of the invention is a mast on the apparatus with a support wire coupled to the boom through the mast and coupled to an anchoring object.

A further aspect of the invention is a winch mounted on the boom and a cable from the winch through a pulley on the carriage to the measuring rod to position the measuring rod vertically.

A still further aspect of the invention is a brake connected to a brake cable to lock and unlock the measuring rod for vertical movement.

Another aspect of the invention is a boom made of a three leg truss and a carriage configured to travel on the three leg truss.

Another aspect of the invention is a boom made of a truss with at least two legs and a carriage configured to travel on two legs.

A further aspect of the invention is a carriage configured to travel on the boom and support the measuring rod vertically.

A still further aspect of the invention is a positioning rod to position the carriage on the boom.

Another aspect of the invention is a support carriage adapted to travel on the boom and configured with a support rod to support the boom.

A further aspect of the invention is an apparatus adapted to measure characteristics of air quality, weather, water quality, soils, sediments, volcanic gases and hydrothermal fluids.

A still further aspect of the invention is an apparatus adapted to accommodate sensors including a particle collector, an air sample collector, a diffusive sampler, a thermometer, a psychrometer, a solar radiation detector, a barometer, an air speed indicator, a Nansen-type bottle, an alpha sampler, a pressure-valve sampler, an automated ISCO-type pump sampler, a gravity sediment corer with a core-catcher, an Eckman-type dredge, and an all-plastic Nansen-type bottle.

Another aspect of the invention is a method of using a portable apparatus for measuring a hydraulic feature to perform measurements of a hydraulic feature.

A further aspect is a method of using a support carriage with a support rod to support the boom of a portable apparatus for measuring characteristics of a hydraulic feature.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

BRIEF DESCRIPTION OF THE INVENTION

Referring more specifically to the drawings, for illustrative purposes the present invention is embodied in the apparatus generally shown in FIG. 1 through FIG. 14. It will be appreciated that the apparatus may vary as to configuration and as to details of the parts, and that the method may vary as to the specific steps and sequence, without departing from the basic concepts as disclosed herein. The term boom is used to denote an extended structure that supports objects.

Figure 1:
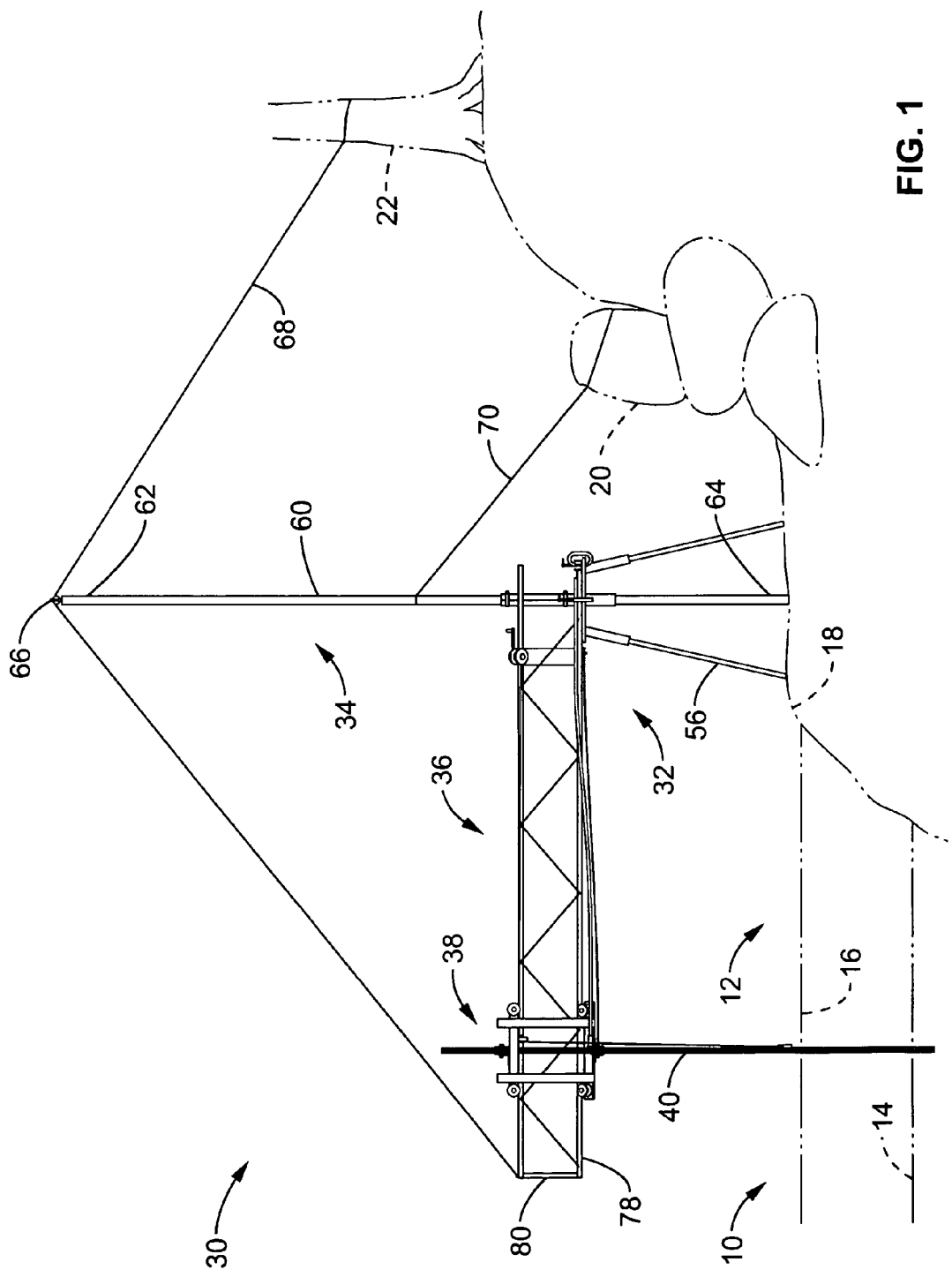
FIG. 1 is a side view of a portable apparatus for measuring a hydraulic feature according to an embodiment of the invention, shown assembled and positioned at a hydraulic feature site.
Figure 2:
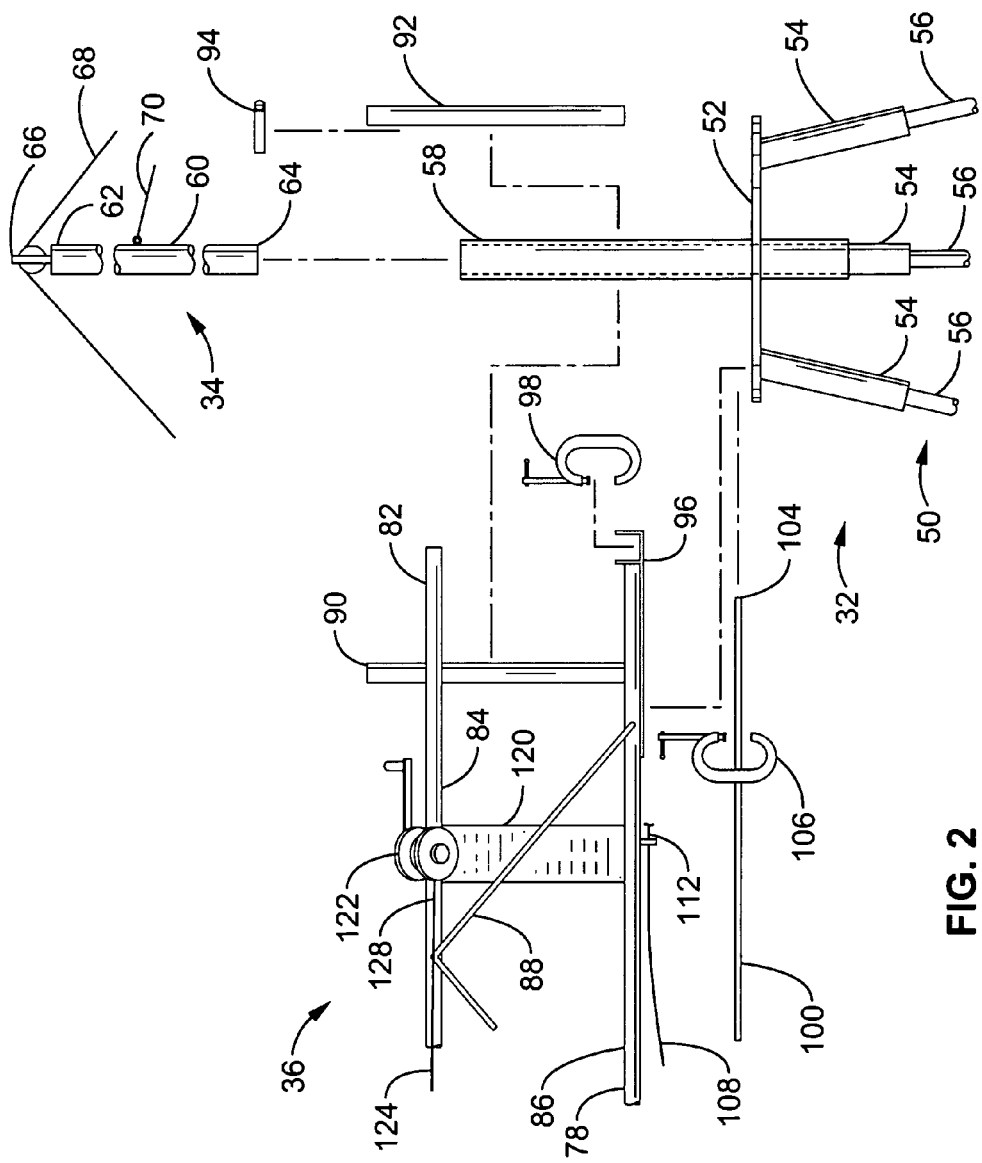
FIG. 2 is an exploded view of a platform, mast and swing boom portion of the apparatus shown in FIG. 1.
Figure 3:
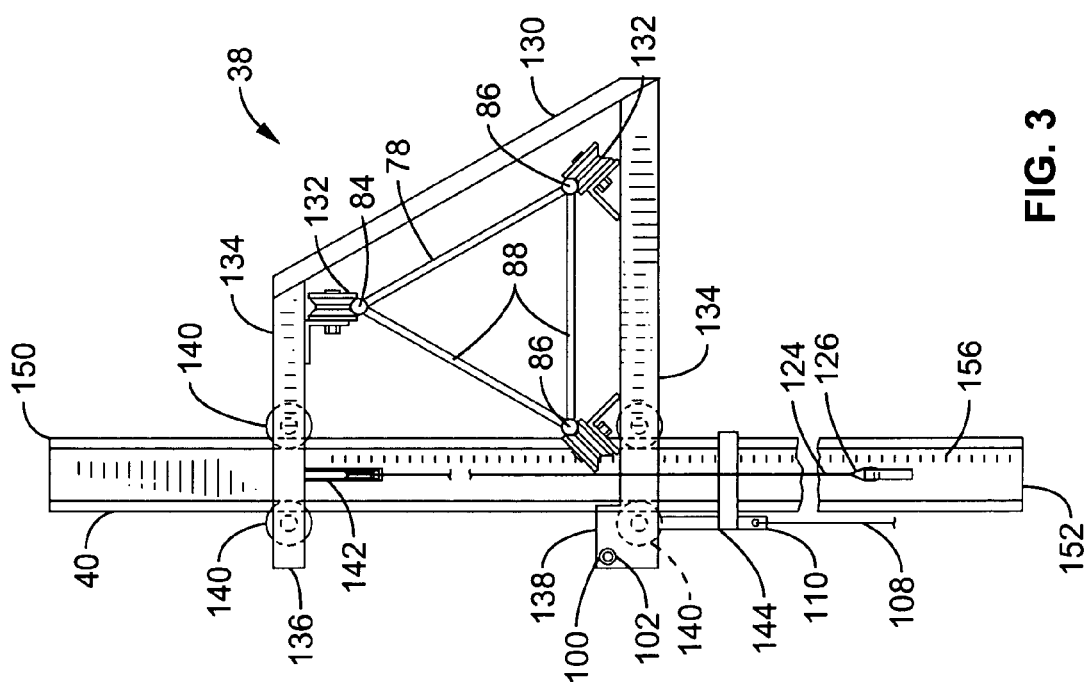
FIG. 3 is a detailed end view of an embodiment of a carriage assembly and a measuring rod portion of the apparatus shown in FIG. 1.
Figure 4:
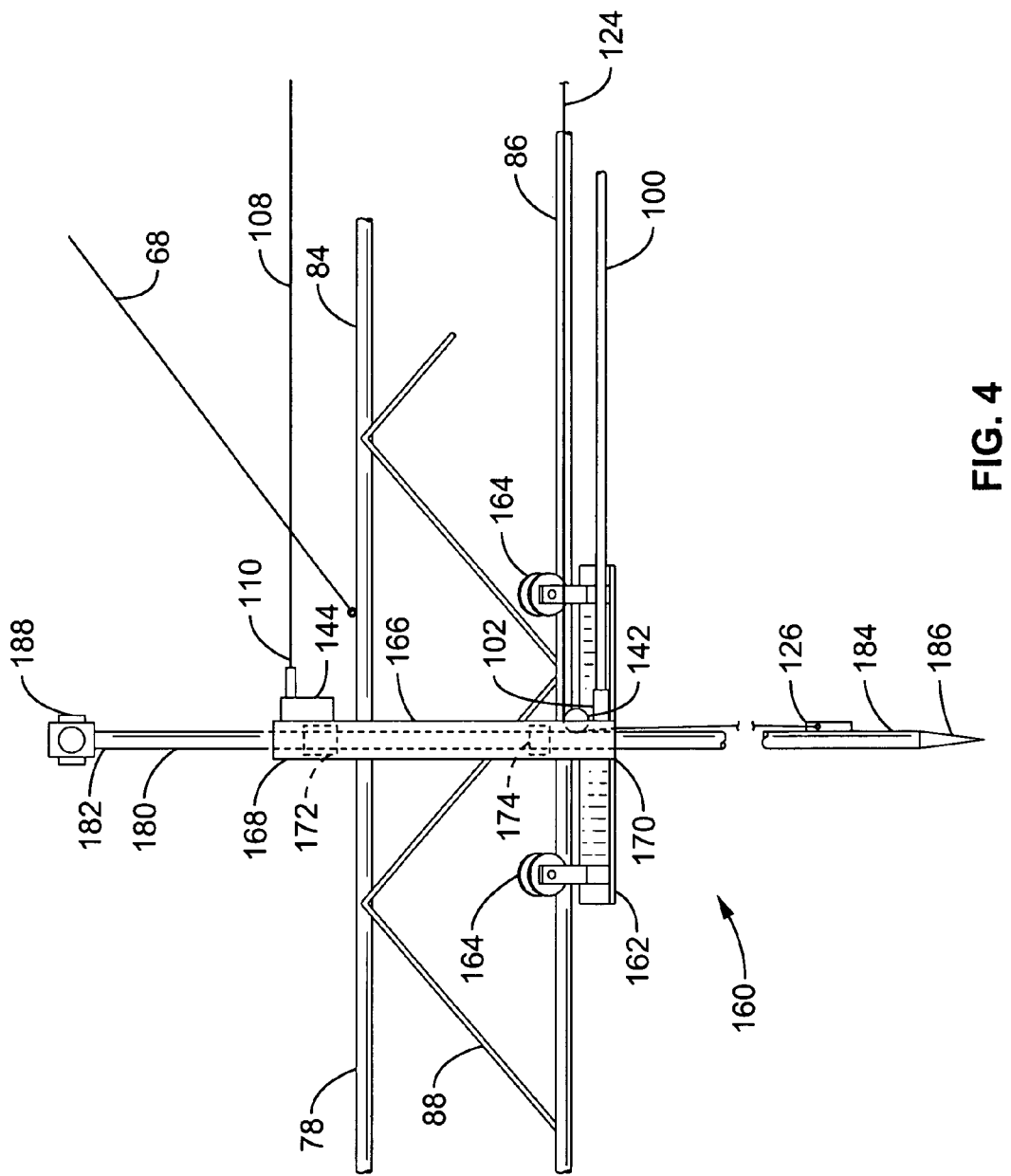
FIG. 4 is side view of another embodiment of a carriage assembly and a measuring rod portion of the apparatus shown in FIG. 1.

FIG. 1 through FIG. 4 show a portable apparatus for measuring a hydraulic feature. FIG. 1 illustrates a hydraulic jump site with the invention assembled for measurement. FIG. 2 through FIG. 4 illustrate details of the major components of the portable apparatus.

In FIG. 1, a typical hydraulic feature site 10 is illustrated in phantom. Hydraulic site 10 has swift moving water, such as a river, flowing over obstacles forming a hydraulic jump 12 designated by two water surface lines 14 and 16 at different elevations. The ground 18 adjacent to hydraulic jump 12 is typically rugged, uneven and of different terrain conditions including solid rock, loose rock, large boulders, sand or soil. Large objects such as boulders 20 or trees 22 may be present at hydraulic feature site 10 and can be used as anchoring objects.

An assembled portable apparatus 30 is shown positioned adjacent to hydraulic jump 12. The primary components of apparatus 30 are designated as a platform assembly 32, a mast support system 34, a swing boom assembly 36, a carriage assembly 38, and a measuring rod 40. Further details of platform assembly 32, mast support system 34 and swing boom assembly 36 are described in FIG. 2. Further details of carriage assembly 38 and measuring rod 40 are described in FIG. 3 and FIG. 4. In operation, swing boom assembly 36 is mounted on platform assembly 32 and further supported through mast 34. Swing boom assembly 36 supports carriage assembly 38 and is positioned in a desired orientation over hydraulic jump 12. Carriage assembly 38 is configured to travel on swing boom 36, supports measuring rod 40, and is positioned at a desired position on swing boom assembly 36. Measuring rod 40 is positioned at a desired elevation over hydraulic jump 12 for measurement.

Referring now to FIG. 1 and FIG. 2, platform 32 consists of a tripod 50 with a horizontal plate 52 and three leg sockets 54 welded to the bottom of plate 52. Tripod 50 is supported on adjustable legs 56 attached to leg sockets 54. In a preferred embodiment (not shown), legs 56 consisted of coupled sections for portability. Legs 56 have interchangeable ends (not shown) for different terrain surfaces. Examples of interchangeable ends are a point, a flat end, a flat pad and an articulating pad.

Referring to FIG. 2, tripod 50 has center tube 58 through the center of plate 52. Center tube 58 performs as a pivot post for swing boom assembly 36 and support for mast 34. Tripod 50 and legs 56 are made of lightweight material such as aluminum, aluminum alloy, titanium or carbon fiber for portability.

Mast assembly 34 has a mast 60 that provides stability for the tripod 50 and swing boom assembly 36. Mast 60 has top end 62 and a bottom end 64 and is inserted vertically through center tube 58 so that bottom end 64 is supported on the ground 18 (see FIG. 1). Top end 62 of mast 60 has a pulley 66 that supports a support cable 68 that is coupled to an object such as a tree 22.(see FIG. 1) at one end and is coupled to swing boom assembly 36 at the other end. Additional anchoring cable(s) 70 attach to mast 60 and to anchoring objects such as rocks 20. The tension of the support cables 68, 70 can be adjusted during operation, i.e. with a turnbuckle (not shown), to maintain swing boom assembly 36 in a horizontal position. In a further embodiment (see FIG. 5), weights such as rocks or bags of water can be suspended from platform 52 for added stability.

Referring again to FIG. 1 and FIG. 2, the swing boom assembly 36 is adapted from a light-weight triangular truss 78, such as used for portable display structures, with a distal end 80 (shown in FIG. 1) and a proximal end 82. Upper leg 84 and lower legs 86 are interconnected with struts 88. In a preferred embodiment, truss 78 is comprised of multiple sections that are assembled in the field for portability. Triangular truss 78 can have different cross section dimensions depending on the application. In one embodiment the distance between legs 84, 86 is about 9 inches. In other embodiments, the distance between legs 84, 86 is about 6, 10, 12, or 14 inches. In a further embodiment, the outside diameter of legs 84, 86 is about one inch. In a still further embodiment, the outside diameter of legs 84, 86 is up to about two inches. In other embodiments, the cross section truss 78 is two legs or four legs. A split sleeve base 90, adapted to mate with the center tube 58, is welded to truss 78 near the proximal end 82. The split sleeve base 90 is made from angle iron, split pipe or other material adapted to articulate on center tube 58 and support a cantilevered boom. A concave split sleeve cap 92 is configured to mate with the split sleeve base 90 so that the truss 78 will articulate on center tube 58 on the platform 52. One or more circular clamps 94, such as a hose clamp, secure the split sleeve cap 92 to the split sleeve base 90 around center tube 58. An index plate 96 is welded to leg 86 at the proximal end 82 of truss 78 and is configured to slide on horizontal plate 52 of tripod 50 as truss 82 articulates. In a preferred embodiment, the horizontal plate 52 has reference markings and the index plate 96 has an indicator to align with the reference markings. A C-clamp 98 or other securing device is used to secure the index plate 96 to the horizontal plate 52 when the swing boom assembly 36 is oriented in a desired position.

A positioning rod 100 configured to move carriage assembly 38 on swing boom assembly 36 has a distal end 102 coupled to carriage assembly 38 (see FIG. 3 and FIG. 4) and a proximal end 104 shown here. Proximal end 104 of positioning rod 100 is adapted to be secured to plate 96 with a C-clamp 106 or similar securing device when carriage assembly 38 is in a desired position on swing boom assembly 36.

A brake cable 108 has a distal end 110 coupled to the carriage assembly 38 (see FIG. 3 and FIG. 4) and a proximal end 112, shown here, slidingly coupled to truss 78 near proximal end 82.

A winch plate 120 supports a winch 122 and is mounted to truss 78 near proximal end 82. Winch cable 124 has a distal end 126 and a proximal end 128 with distal end 126 coupled to measuring rod 40 as shown in FIG. 3 and FIG. 4. Proximal end 128 of winch cable 124 is attached at winch 122.

FIG. 3 illustrates carriage assembly 38 as a carriage frame 130 mounted on upper leg 84 and lower legs 86 of truss 78 using support wheels 132. Carriage frame 130 is made from aluminum or other lightweight stiff material and encloses truss 78. Carriage frame 130 can be configured to mount on a truss 78 of different cross section dimensions and different leg diameters. Support wheels 132 are configured with a concave contact surface and positioned to roll on the outside of legs 84, 86 without interfering with struts 88. The carriage frame 130 has a vertical bracket 134 with upper end 136 and lower end 138 that supports measuring rod 40, also known as a Vertical Measuring Rod (VMR 40). Upper end 136 and lower end 138 of vertical bracket 134 have guide wheels 140, shown partially in phantom, to align VMR 40 vertically and resist lateral forces while allowing VMR 40 to move vertically. Upper end 136 of vertical bracket 134 supports pulley 142 that supports winch cable 124. The distal end 102 of positioning rod 100 is shown attached to the lower end 138 of vertical bracket 134 and is adapted for an operator to move carriage assembly 38 along truss 78 from the proximity of platform 32 (see FIG. 2) Lower end 138 of vertical bracket 134 has spring-loaded friction brake 144 that articulates on a horizontal axis and contacts and secures VMR 40 in a desired elevation relative to vertical bracket 134. The details of brake 144 are not shown but can be of several designs, i.e. a spring-loaded bicycle wheel rim brake, spring-loaded clothespin, or spring-loaded clamp with a friction pad, as are well known in the art. Distal end 110 of brake cable 108 is coupled to brake 144 and configured so that brake 144 is released from VMR 40 when tension is applied to brake cable 108.

VMR 40 has a top end 150 and measuring end 152. Distal end 126 of winch cable 124 is coupled to VMR 40 near measuring end 152 and runs vertically through pulley 142, then horizontally to winch 122 (shown in FIG. 2). VMR 40 is raised by first placing tension on brake cable 108 to release brake 144, then retracting cable 124 with winch 122. VMR 40 is lowered by gravity by putting tension on brake cable 108 to release brake 144 and letting out cable 124 with winch 122.

IN FIG. 3, VMR 40 is a long hollow tube of a stiff material, such as aluminum alloy or steel, to withstand flexing due to lateral water pressure. The measuring end 152 is configured to submerge in a hydraulic feature. In the embodiment shown here, the cross section of VMR 40 is a hollow, elongated hexagon and vertical bracket 134 is configured to position the elongated portion of VMR 40 approximately parallel to the water flow. In a preferred embodiment, the VMR 40 is made of a plurality of coupling sections (not shown) for portability. In a further embodiment, reference marks 156 are placed on the surface of VMR 40 to allow visual observation of the distance of the measuring end 154 from carriage frame 130. In another embodiment (not shown) weights are added to the top of VMR 40 to aid gravity lowering.

FIG. 4 illustrates a side view of a preferred embodiment of another carriage assembly, designated here as 160. Carriage frame 162 is configured as a rectangular platform that is positioned below the lower legs 86 of truss 78 and supported with support wheels 164. Support wheels 164 are configured with concave contact surfaces and adapted to contact the two lower legs 86 on their upper and outside surface and without interference with struts 88. Carriage frame 162 does not enclose upper leg 84 and does not interfere with a support cable 68 coupled to upper leg 84 of truss 78, thus allowing multiple support cables 68 to be attached to upper leg 84. Further, carriage 160 can operate without interference when additional sections of horizontal truss 78 and additional support cables 68 are added. In another embodiment (not shown), carriage frame 162 is adapted to accommodate trusses of different cross section dimensions and different diameters of legs.

Carriage frame 162 has support bracket 166 mounted on one side of carriage frame 162. Support bracket 166 has an upper end 168 and a lower end 170. An upper bushing 172 is mounted on upper end 16B of support bracket 166 and a lower bushing 174 is mounted on lower end 170 of support bracket 166 and are configured to allow a measuring rod 180 to slide vertically. A friction brake 144 similar to that described previously in FIG. 3, is shown schematically configured to articulate on a vertical axis and is mounted on upper end 168 of support bracket 166 coupled to distal end 110 of brake cable 108. Distal end 102 of positioning rod 100 is shown here mounted on lower end 170 of support bracket 166. Pulley 142 for winch cable 124 is shown here mounted on lower end 170 of support bracket 166. Winch 122 (shown in FIG. 2) would be repositioned accordingly to a lower position on winch plate 120 at proximal end 82 of truss 78.

Measuring rod 180 has a tubular cross section with upper end 182 and measuring end 184. Distal end 126 of winch cable 124 is coupled near measuring end 184 and runs vertically through pulley 142, then horizontally to winch 122 (see FIG. 2). Measuring end 184 of measuring rod 180 is shown fitted with a taper 186 that allows improved visual observation when taper 186 contacts the surface of the water. Taper 186 is adapted to more accurately contact the channel bottom beneath the hydraulic feature to measure the depth of the channel and fit into narrow rock fissures on the channel bed. Positioning of carriage 160 on truss 78 and adjusting elevation of measuring rod 180 is accomplished as previously described in FIG. 3.

In a further embodiment (see FIG. 8), measuring end 184 is configured with one or more ports to accommodate sensor devices to measure characteristics of a hydraulic feature. In another embodiment, measuring end 184 is configured with sensors to measure characteristics of a hydraulic feature. Examples of sensors accommodated include differential pressure sensors, time domain reflectometers current meters such as propeller, electromagnetic, and acoustic Doppler velocimeters, digital cameras and video cameras. In one embodiment, output signals from the sensors are routed through wires (not shown for clarity) in the hollow measuring rod 180 that exit measuring rod 180 at upper end 182 and connect to a data logger or data acquisition board mounted on carriage 160 that can be interfaced by cable, radio or infrared signal with a data receiving device, such as a laptop computer (not shown), typically positioned near platform 32.

In a further embodiment, upper end 182 of measuring rod 180 is adapted to accommodate a survey reference instrument 188 such as an transit prism, 360 degree prism or GPS receiver. In another embodiment (not shown), weights are added to the upper end 182 of measuring rod 180 to aid gravity lowering.

It is contemplated in other embodiments (not shown) that portable apparatus 30 (shown in FIG. 1) and measuring rod 180 accommodate sensors in other positions, such as near the rod top, bolted on the outside, on the mast, on the boom, etc., and are adapted accommodate sampling devices. Examples of uses contemplated are measuring and sampling devices for air quality, weather, water quality, soils, sediments, volcanic gases and hydrothermal fluids. In a further embodiment, (not shown), portable apparatus 30 is adapted to accommodate air quality monitoring equipment including a particle collector, an air sample collector and a diffusive sampler. In a still further-embodiment (not shown), portable apparatus 30 is adapted to accommodate weather measurement equipment including a thermometer, a psychrometer, a solar radiation detector, a barometer and an air speed indicator. In another embodiment, (not shown), portable apparatus 30 is adapted to accommodate water quality monitoring equipment including, a Nansen-type bottle, an alpha sampler, a pressure-valve sampler, and an automated ISCO-type pump sampler. In a further embodiment, (not shown), portable apparatus 30 is adapted to collect sediment with a gravity sediment corer with a core-catcher or an Eckman-type dredge. In a still further embodiment, (not shown), portable apparatus 30 is adapted to accommodate acidic hydrothermal fluid sampling with an all-plastic Nansen-type bottle.

Figure 5:
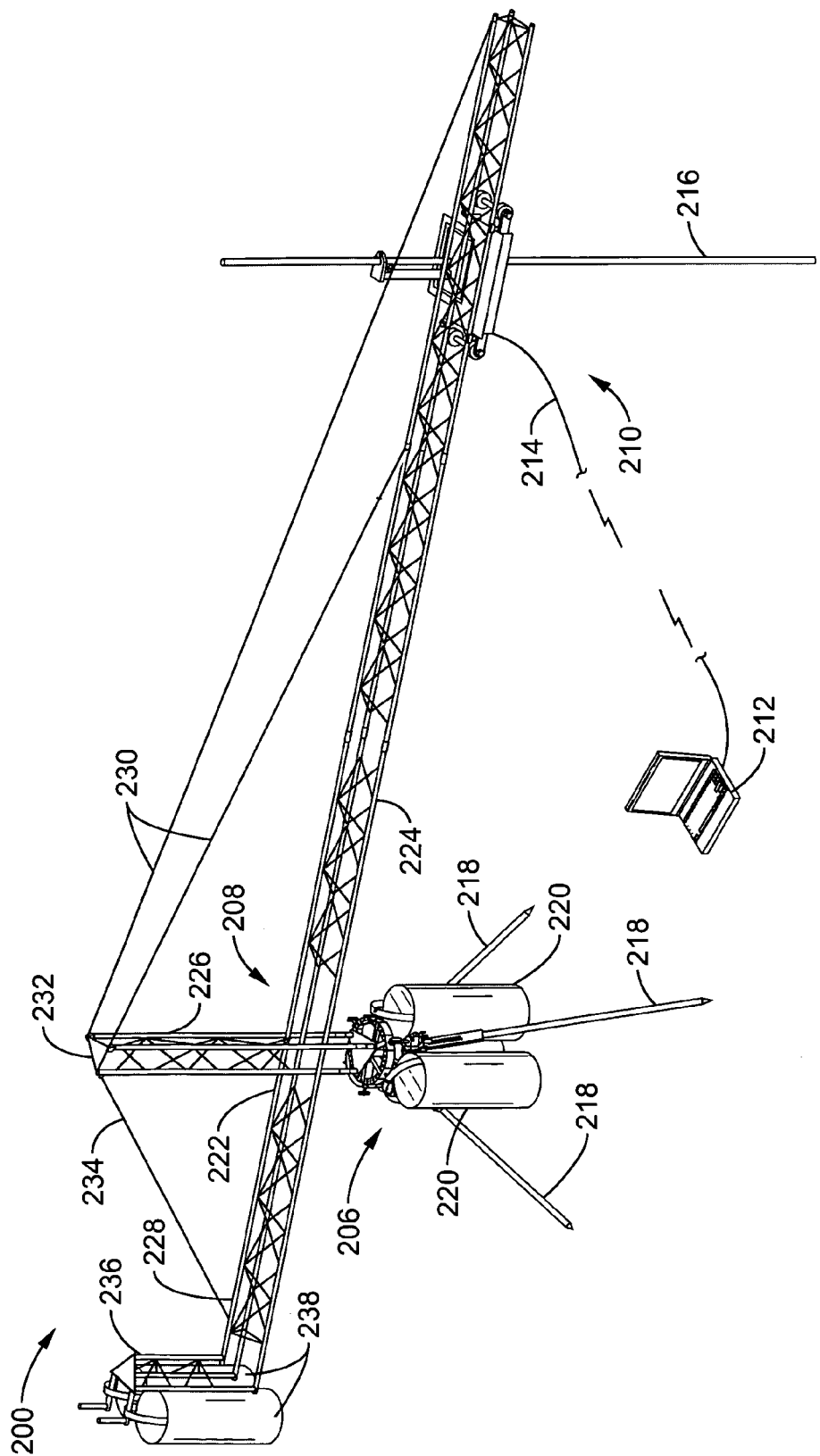
FIG. 5 is perspective view of an assembled portable robotic apparatus for measuring a hydraulic feature according to an embodiment of the invention.

FIG. 5 through FIG. 11 illustrate a portable robotic apparatus, generally designated as 200, for measuring hydraulic features in rivers or streams. In FIG. 5, portable robotic apparatus 200 is comprised of five primary systems; a leveling platform 206, a boom structure 208, an automated carriage 210 connected to a controller 212 via signals 214, and supporting a Vertical Measuring Rod (VMR) 216. Details of leveling platform 206 are further illustrated in FIG. 6 and FIG. 7. Details of automated carriage 210 are illustrated in FIG. 8 through FIG. 11.

In FIG. 5, leveling platform 206, mounted on legs 218, is the support for assembled portable robotic apparatus 200. Stabilizing weights 220, in the form of bags of water, are shown suspended from leveling platform 206. Stabilizing weights 220 can also be in the form or rocks or heavy objects and supported by nets or straps (not shown). Boom structure 208, consists of a four-way hub 222, mounted on leveling platform 206, and coupling a swing boom 224, a mast 226 and a counterweight boom 228. One or more support wires 230 connect swing boom 224 to the top of mast 226 at mast top plate 232. Support wires 234 connect counterweight boom 228 to mast top plate 232. support wires 230, 234 have turnbuckles for adjustment. Counterweight boom 228 is shown with a counterweight mast 236. Counterweights 238, in the form of bags of water, are shown suspended from counterweight mast 236. Mesh bags or straps with rocks (not shown) may also be used. Automated carriage 210 is shown positioned on swing boom 224 at a desired position and holding VMR 216 in a vertical position at a desired elevation.

Figure 6:
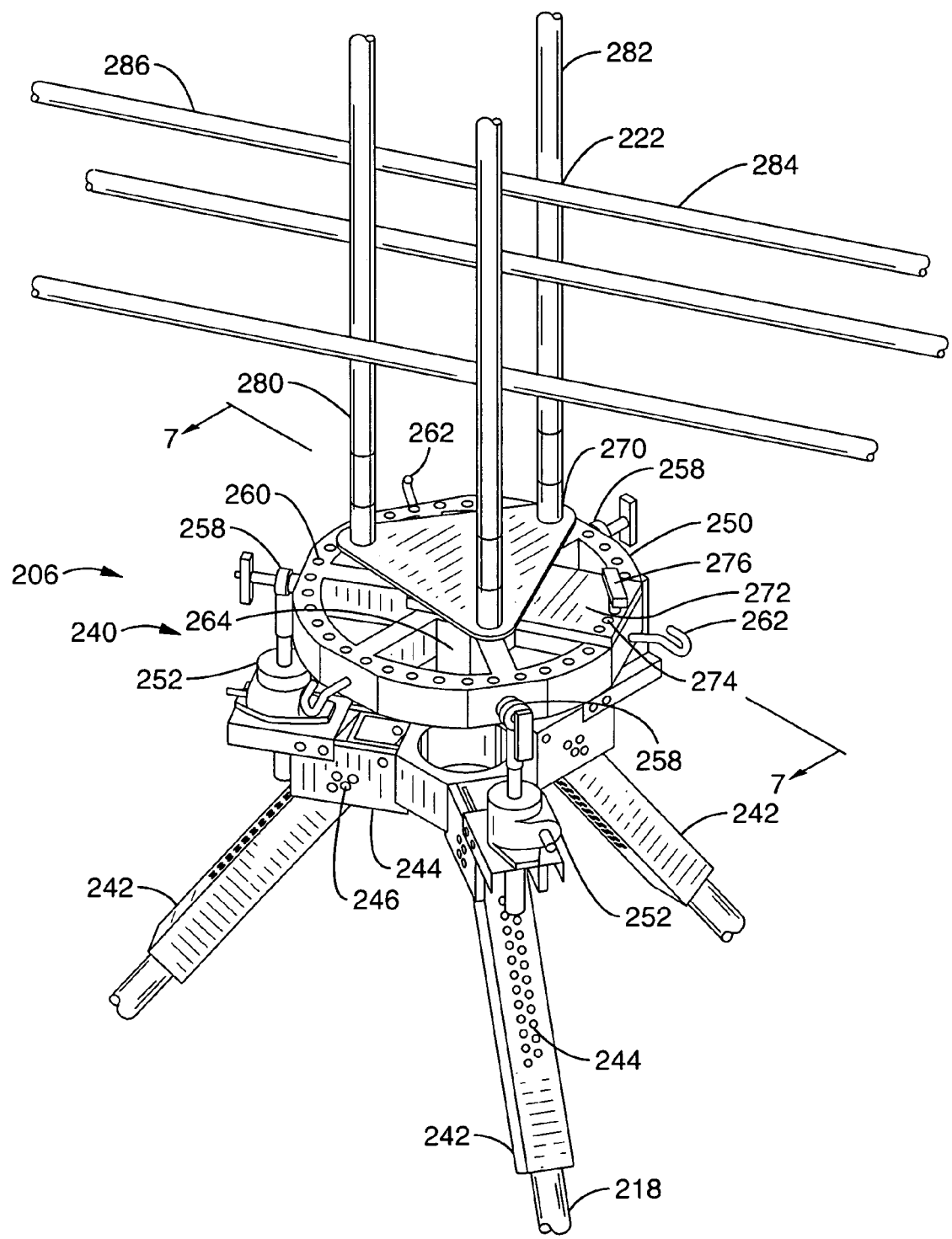
FIG. 6 is a perspective detailed view of the leveling platform portion of the apparatus shown in FIG. 5
Figure 7:
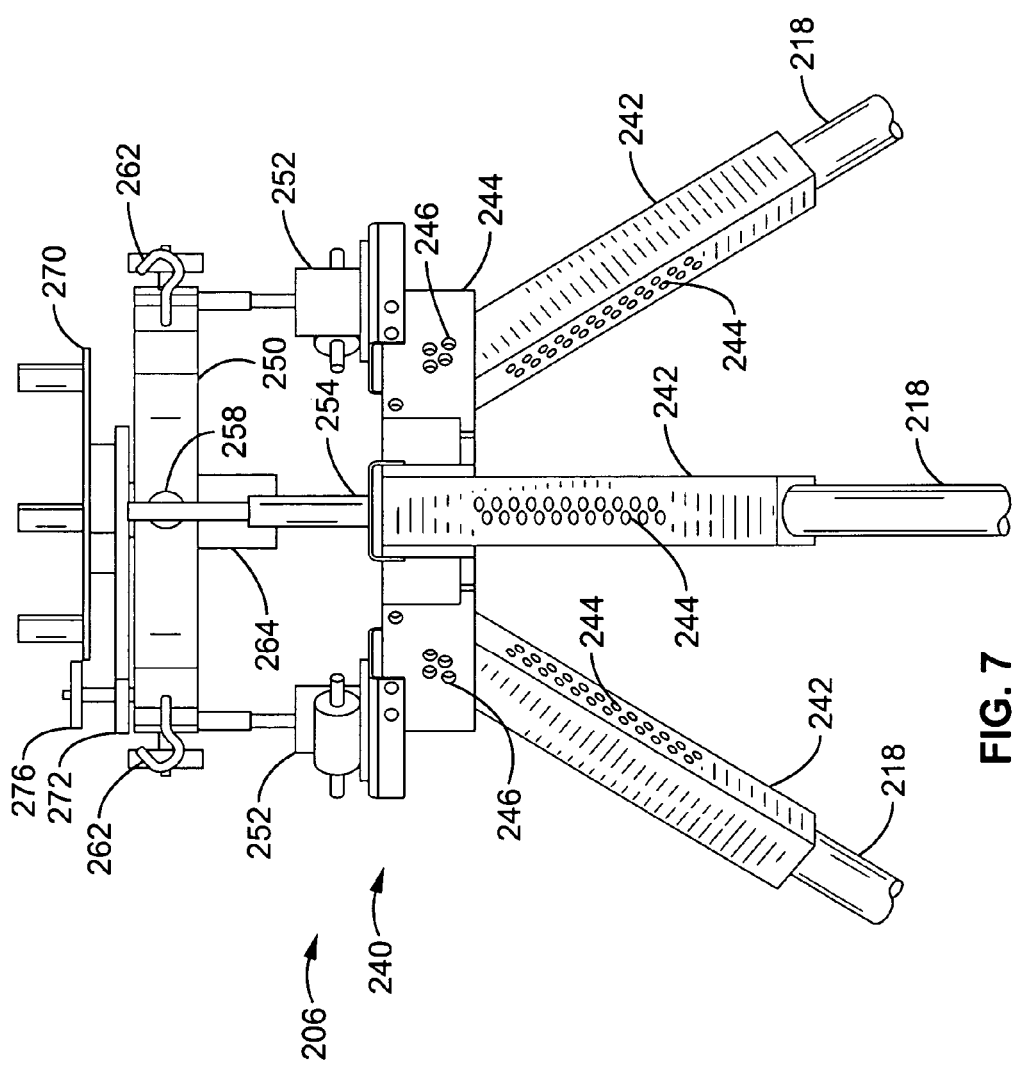
FIG. 7 illustrates the leveling platform shown in FIG. 6 taken at line 7—7.

FIG. 6 and FIG. 7 illustrate the leveling platform 206 shown in FIG. 5 with the view in FIG. 7 taken at line 7—7 in FIG. 6. Leveling platform 206 consists of a leveling tripod 240 having leg sockets 242 with a plurality of apertures 244 at different positions and adapted to mate with an aperture (not shown) in legs 218. The tripod orientation relative to the ground can be quickly adjusted by realigning apertures and securing the position with a lock pin (not shown) through an aligned aperture 244 and a leg aperture. The angle of the leg sockets 242 can also be adjusted by realigning leg sockets 242 with tripod base 244 and securing socket apertures 246 with a lock pin (not shown). Legs 218 are assembled from a plurality of different length sections that can be coupled together and have a selection of leg feet that can be reconfigured depending on terrain conditions (as previously discussed in FIG. 2). Legs 218 are made of sturdy, lightweight materials, such as aluminum, aluminum alloys, titanium or carbon fiber.

Tripod base 244 supports a circular index base 250 on two leveling jacks 252 and a post 254 (shown in FIG. 7), each supported over a leg socket 242. In a preferred embodiment (not shown) post 254 is replaced with a third leveling jack 252. Leveling jacks 252 and post 254 are spaced equidistant on the perimeter of index base 250 and each coupled to index base 250 with a ball joint 258. Other configurations or numbers of leveling jacks 252 can be used in further embodiments. For heavier configurations, leveling jacks 252 can be replaced with fixed support blocks (not shown). Index base 250 can be maintained in a level orientation during repositioning and measurement operations by adjusting one or both leveling jacks 252. In a preferred embodiment, leveling jacks 252 are in the form of screw jacks. In a further embodiment (not shown), leveling jacks 252 have motors and are controlled by controller 212 shown in FIG. 5.

In FIG. 6, Index base 250 has a plurality of evenly spaced index apertures 260 around the perimeter for polar coordinate positioning of the swing boom 224 (shown in FIG. 5). The index base 250 also has three or more hooks 262 on the perimeter to hang weights such as rocks or bags of water 220 (as shown in FIG. 5) for stability. Index base 250 is configured in a wheel and spoke cross-section to help reduce weight.

Referring to FIG. 6 and FIG. 7, Index base 250 has a socket 264 at its center and a tapered roller bearing (not shown) in socket 264. A boom turntable 270 with a vertical spindle (not shown) is positioned in socket 264 and on the tapered roller bearing so it rotates freely. Turntable 270 is configured with an index pointer 272 and with reference apertures 274 adapted to align with the index apertures 260 in the index plate 250. In another embodiment, turntable 270 is configured with a full-cover index plate (not shown) with reference apertures 274. Turntable 270 can be secured in a desired orientation by aligning a reference aperture 274 with a desired index aperture 260 and inserting a spring pin 276. A clamp may be used to provide additionally rigidity when using a full-cover plate.

FIG. 6 illustrates a four-way truss hub 222 with the base leg 280 mounted to turntable 270. The interconnecting struts 88 on four way hub 222 are omitted for clarity. Four-way hub 222 is configured with a vertical mast leg 282 coupled to mast 226, a horizontal swing boom leg 284 coupled to swing boom 224 and a horizontal counterweight leg 286 coupled to counterweight boom 228, all as part of the boom structure 208 shown in FIG. 5. Four way hub 222 and associated booms and masts can be of different cross section dimensions where the legs are, for example, 6, 9, 10, 12, or 14 inches apart. The outside diameter of the legs of four way hub 222 can be about one inch or more. Additionally, the cross section of the booms and masts can be a combination of two legs, three legs or four or more legs. It is contemplated that carriage 160, shown in FIG. 4, can be used on boom structure 208.

Figure 8:
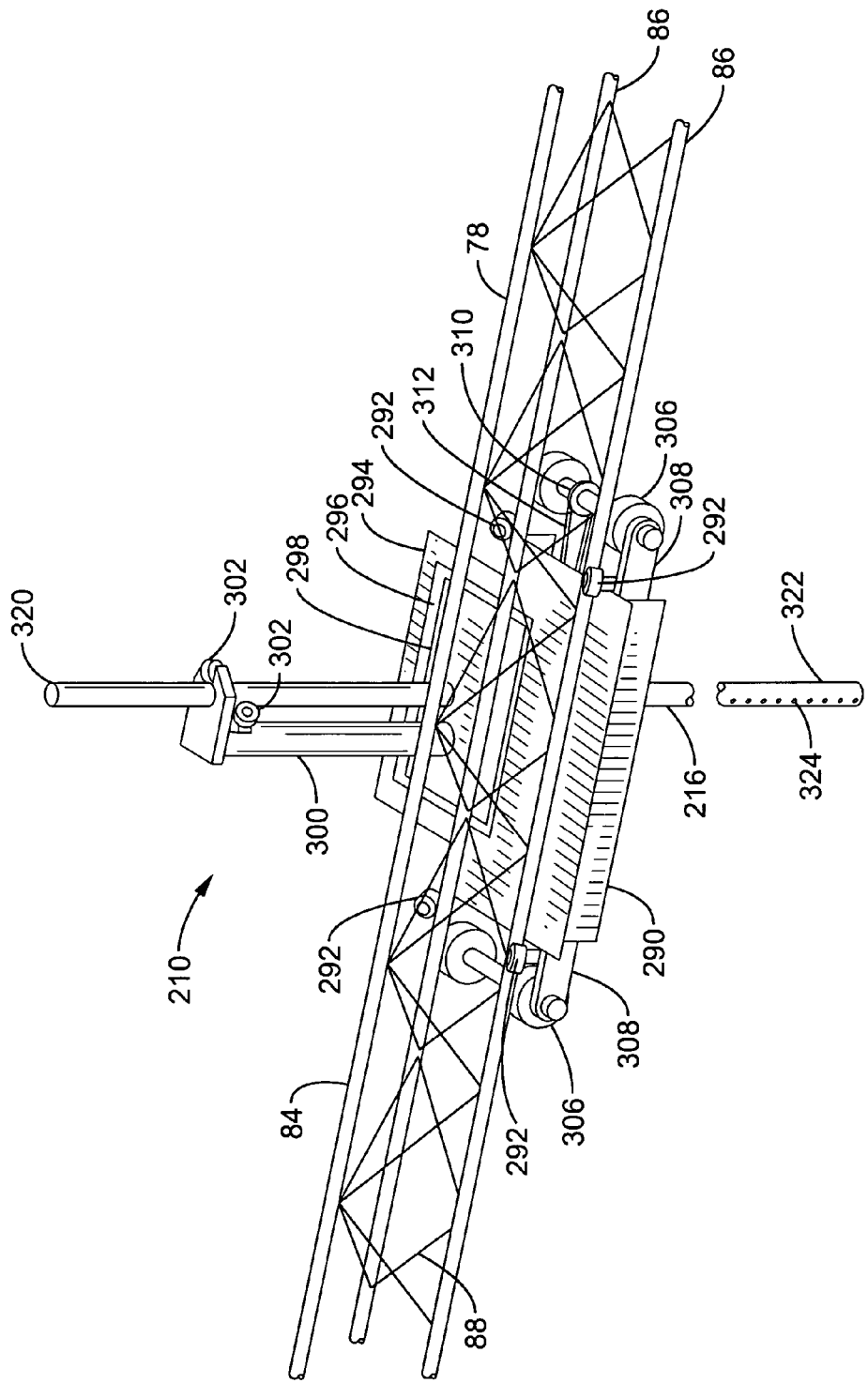
FIG. 8 is a perspective detailed view of an automated carriage and a measuring rod portion of the apparatus shown in FIG. 5.
Figure 9:
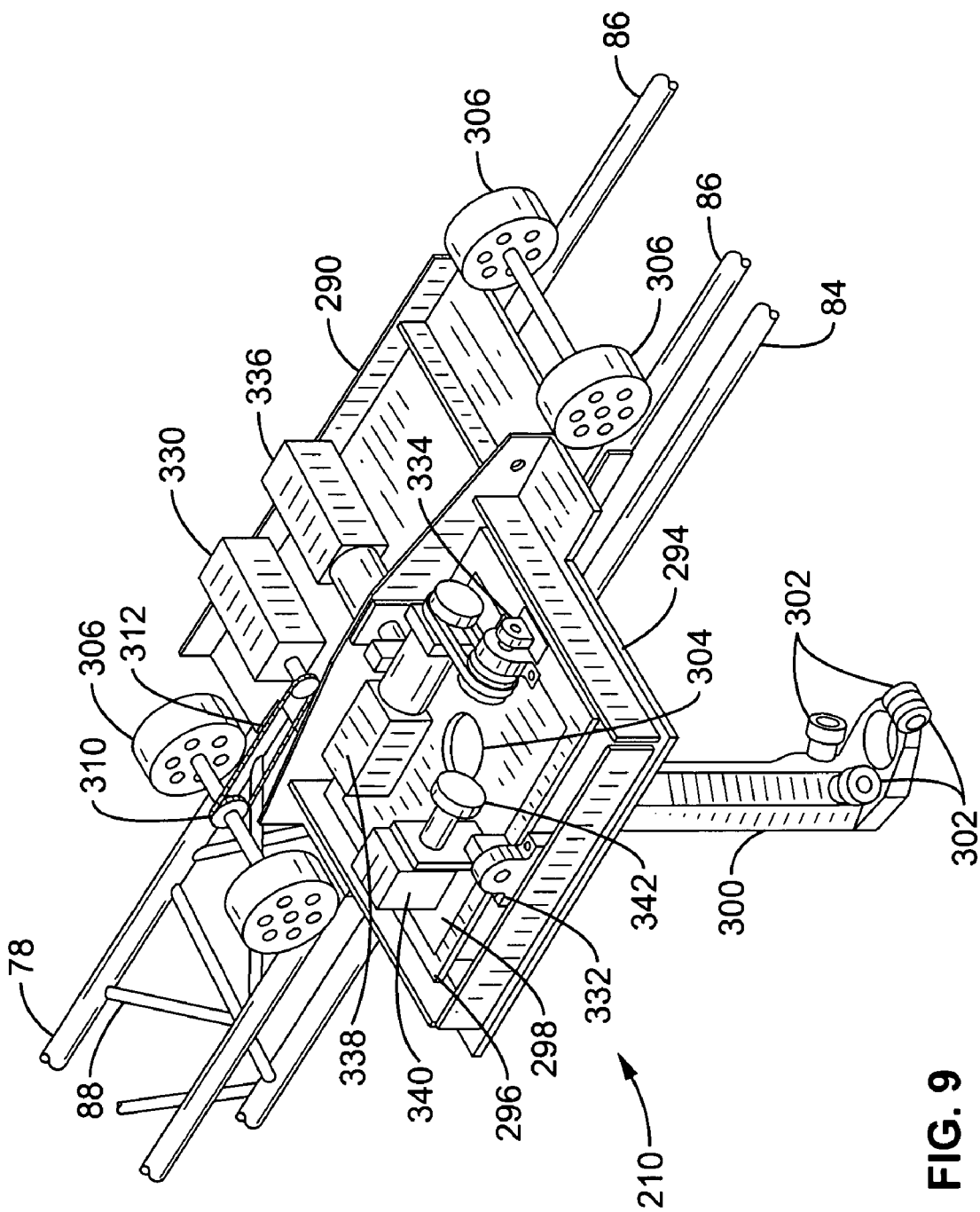
FIG. 9 is a perspective detailed view of the underside of the automated carriage shown in FIG. 8.

FIG. 8 shows a top view and FIG. 9 shows an underside view of an automated carriage 210 as shown in FIG. 5 and configured to travel along two legs of a two, three, or four leg truss 78. Automated carriage 210 is configured as a rectangular carriage frame 290 with spring loaded support wheels 292 mounted to extend up from near the corners of carriage frame 290 and configured to roll on the top and outer surface of the bottom two legs 86 of a truss 78. Support wheels 292 are configured to not interfere with struts 88 or top leg 84 of truss 78.

In FIG. 8 and FIG. 9, a rectangular VMR support frame 294 is mounted on the carriage frame 290 and to one side of three leg truss 78. A counterweight (not shown) can be mounted on the other side of carriage frame 290 to balance automated carriage 210. A gimbal frame 296 is mounted on VMR support frame 294 and a VMR platform 298 mounted on gimbal frame 296. A VMR support mast 300 is mounted on VMR platform 298 and oriented perpendicular to VMR platform 298. Spring loaded guide wheels 302 are shown mounted at the top of VMR mast 300 and configured to hold VMR 216 perpendicular to the VMR platform 296 and resist lateral forces on the VMR 216. Additional guide wheels 302 (not shown for clarity) are mounted at the base of VMR mast. A VMR aperture 304 in VMR platform 298 (see FIG. 9) is aligned with VMR support mast 300 and configured to accommodate VMR 216.

A set of drive wheels 306 are attached at the corners of carriage frame 290 with drive wheel mounts 308 and configured to contact the bottom two legs 86 of the three-leg truss 78 that comprises swing boom 224. At least two drive wheels 306 are coupled to a drive gear 310 and drive chain 312. Drive wheel mounts 308 can also accommodate support wheels 292 as shown in FIG. 8. In a further embodiment (not shown), drive wheel mounts 308 and support wheels 292 are configured to adapt to different cross section dimensions of truss 78 and to different outside diameter truss legs.

In FIG. 8, a Vertical Measuring Rod (VMR) 216 with a tubular cross section is positioned in the VMR aperture 304 (shown in FIG. 9) and secured from lateral movement by guide wheels 302 in mast 300. VMR 216 has an upper end 320 and a lower end 322. In a preferred embodiment, lower end 322 is configured with a plurality of sensors ports 324 to accommodate sensor devices to measure characteristics of a hydraulic feature. Examples of sensors devices include differential pressure sensors, time domain reflectometers current meters such as propeller, electromagnetic, and acoustic Doppler velocimeters, digital cameras and video cameras. In other embodiments (not shown), VMR 216 is configured to accommodate sensors and sampling equipment as previously described in FIG. 4. Output signals from sensors are routed through wires (not shown for clarity) in the hollow VMR 216 and exit the VMR at upper end 320 and connect to infrared or radio transmitters (not shown) on carriage 210. The transmitters connect to a data logger or data collection device (not shown), which typically interfaces with a laptop computer (not shown), positioned in the vicinity of platform 206. In another embodiment, sensor devices can be connected directly to a data collection device through wires or fiber optic cables (not shown). In an exemplary embodiment, the upper end 320 of VMR 216 is adapted to accommodate a survey instrument such as a 360 degree prism or GPS receiver (see FIG. 4).

Referring to FIG. 9, the underside of automated carriage 210 is shown with the VMR 216 omitted for clarity. Drive wheel mounts 308 for drive wheels 306 and support wheels 292 have been omitted for clarity. Drive wheels 306 are positioned to apply traction to the lower surface of the bottom two legs 86 of the three-leg truss 78. Drive motor 330 is mounted on carriage frame 290 and coupled to at least two drive wheels 306 through drive gear 310 and drive chain 312. Drive motor 330 is configured to be controlled by a controller 212 (as shown in FIG. 5 and described below). In other embodiments, the drive system consists of gears, belts or direct drive motors.

VMR support frame 294 extends horizontally to one side of carriage frame 290. VMR support frame 294 supports a two axis gimbal frame 296 on a pair of aligned bearings 332 (one not shown for clarity). Gimbal frame 296 supports VMR platform 298 on a pair of aligned bearings 334 (one not shown for clarity). A first gimbal motor 336 is mounted on carriage frame 290 and adapted to align with bearing 332 and rotate gimbal frame 296 with respect to VMR support frame 296. A second gimbal motor 338 is mounted on VMR platform 298 and is adapted to align with bearing 334 and rotate VMR platform 298 with respect to gimbal frame 296. In one embodiment, gimbal motors 336, 338 are configured to be controlled by a controller 212 (described below). In another embodiment (not shown), a level controller is mounted on VMR platform 298 and connected to motors 336, 338 to provide self leveling of VMR platform 298.

A VMR positioning motor 340 is mounted on the underside of VMR platform 298 and drives a traction wheel 342 positioned adjacent the VMR aperture 302 in VMR platform 298. Traction wheel 342 is configured to maintain contact with VMR 216 (shown in FIG. 8) and move VMR 216 in both directions vertically. Traction wheel 342 serves as a brake to secure VMR 216 when in a desired elevation. VMR positioning motor 340 is configured to be controlled by a controller 212. In a further embodiment (not shown), traction wheel 342 is a pinion gear and VMR 216 is provided with a rack (linear gear teeth) to mate with the pinion gear. In another embodiment (not shown), a second VMR motor and traction wheel is adapted to rotate VMR 216 to change its orientation.

Referring back to FIG. 5, a controller 212, such as a laptop computer is connected to automated carriage 210 through radio or infrared connection 214 and is adapted to control drive motor 330, gimbal motors 336, 338 and VMR positioning motor 340. In another embodiment, controller 212 is also a data logger adapted to receives data signals from VMR sensors installed in VMR 216. Controller 212 may also be configured to receive operator input for calculating swing boom 224 orientation, and positioning automatic carriage 210 and VMR 216. In one embodiment, controller 212 receives orientation signals from a level indicator (not shown) mounted on the VMR platform 298. In another embodiment, connection 214, shown in FIG. 5, is wire or fiber optic cable. In a further embodiment, controller 212 is adapted to be waterproof. Power for automated carriage 210 is provided by battery packs (not shown in FIG. 9 for clarity) coupled to carriage frame 290. In another embodiment, power is provided to the automated carriage 210 through wires connected to a remote power source (not shown). In a still further embodiment, the components of automated carriage 210 are adapted to be waterproof.

In other contemplated embodiments, carriage 210 may share non-automated features with carriage 38 (described previously in FIG. 3) or carriage 160 (described previously in FIG. 4). In one example, carriage 210 is equipped with a positioning rod 100 instead of drive motor 330 and associated drive train. In a further example, carriage 160 (see FIG. 4) is equipped with a gimbal leveling system. In another example (not shown), automated carriage 210 is equipped with a safety cable that can be used to retrieve the carriage in case of power or equipment failure.

Figure 10:
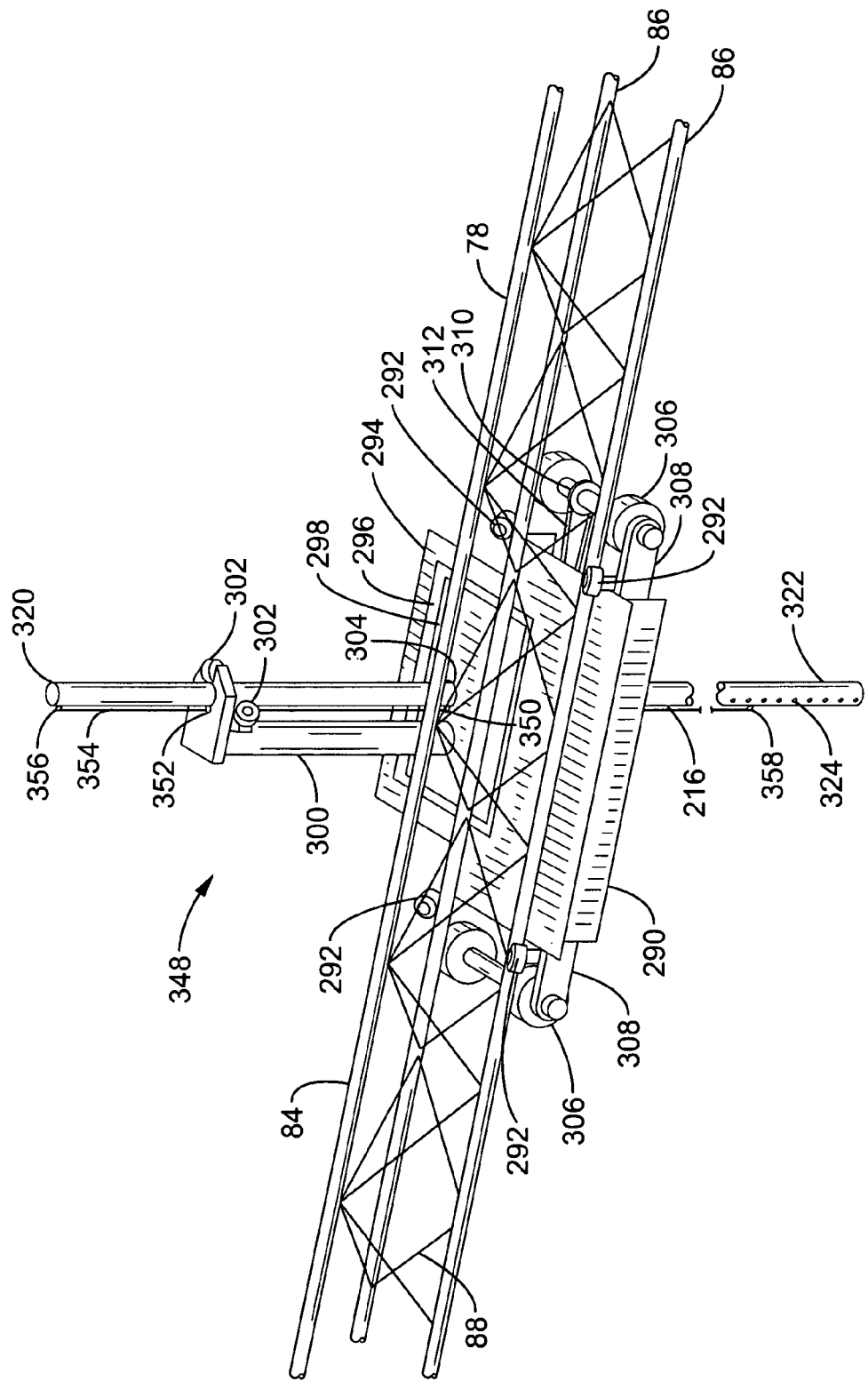
FIG. 10 is a perspective detailed view of an alternative embodiment of an automated carriage and a measuring rod portion of the apparatus shown in FIG. 5.
Figure 11:
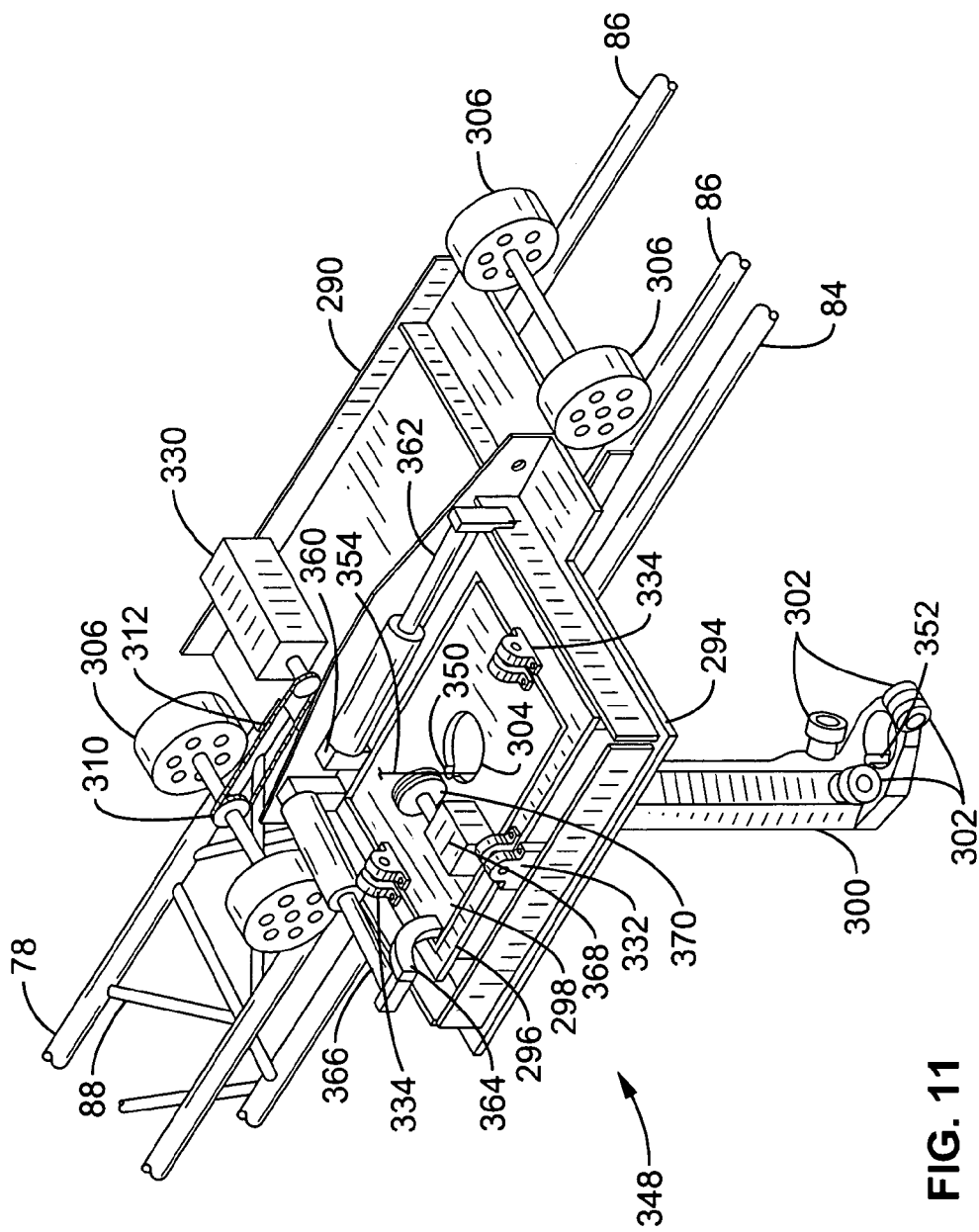
FIG. 11 is a perspective detailed view of the underside of the automated carriage shown in FIG. 10.

FIG. 10 is a top view and FIG. 11 is a bottom view of another embodiment of an automated carriage generally designated as 348. In this embodiment, carriage frame 290 support wheels 292 and drive wheels 306 are configured the same as carriage 210 shown in FIG. 8. VMR support frame 294 is mounted to one side of carriage frame 290. A gimbal frame 296 is mounted on VMR support frame 294 and a VMR platform 298 mounted on gimbal frame 296. A VMR support mast 300 is mounted on VMR platform 298 and oriented perpendicular to VMR platform 298. Spring loaded guide wheels 302 are shown mounted at the top of VMR mast 300 and configured to hold VMR 216 perpendicular to the VMR platform 296 and resist lateral forces on the VMR 216. Additional guide wheels 302 (not shown for clarity) are mounted at the base of VMR mast. A notch aperture 350 is positioned in aperture 304 in VMR platform 298 (see FIG. 11). A notch aperture 352 is aligned with notch aperture 350 and positioned in VMR support mast 300. A bow cable 354 is attached to MVR rod 216 at upper coupling 356 near top 320 of VMR rod 216 and at lower coupling 358 near lower end 322 of VMR rod 216. In one embodiment, upper and lower coupling 356, 358 are adjustable eyebolts in VMR rod 216. In another embodiment (not shown), upper and lower coupling 356, 358 are collars mounted in grooves in VMR 216 to allow rotation of VMR 216. A turnbuckle or other adjusting feature may be coupled with bow cable 354. A washer or similar object (not shown) may be mounted near either end of bow cable 354 as a vertical stop. In further embodiments, notch apertures 350, 352 are aligned in different orientations or are omitted. In a still further embodiment (not shown), guide wheels for bow cable 354 are aligned with or replace notch apertures 350, 352.

Referring to FIG. 11, the underside of automated carriage 348 is shown with the VMR 216 omitted for clarity. Drive wheel mounts 308 for drive wheels 306 and support wheels 292 have been omitted for clarity. Drive motor 330 is mounted on carriage frame 290 and coupled to at least two drive wheels 306 as shown previously in FIG. 9.

VMR support frame 294 extends horizontally to one side of carriage frame 290. VMR support frame 294 supports a two axis gimbal frame 296 on a pair of aligned bearings 332 (one not shown for clarity). Gimbal frame 296 supports VMR platform 298 on a pair of aligned bearings 334. A first gimbal bracket 360 is coupled to gimbal frame 296. First gimbal actuator 362 is mounted on carriage frame 290 and adapted to rotate gimbal frame 296 with respect to VMR support frame 296. A second bracket 364 is mounted on VMR platform 298. Second gimbal actuator 366 is mounted on gimbal frame 296 and is adapted to rotate VMR platform 298 with respect to gimbal frame 296. In one embodiment, gimbal actuators 362, 366 are configured to be controlled by a controller 212 (described below).

A VMR motor 368 is mounted on the underside of VMR platform 298 and drives a cable sheave 370 positioned adjacent the VMR aperture 302 and notch aperture 350 in VMR platform 298. Bow cable 354 (see FIG. 10) is configured to loop around cable sheave 370 and move VMR 216 in either direction vertically. Cable sheave 370 and VMR motor 368 serve as a brake to secure bow cable 354 and VMR 216 when in a desired elevation. VMR motor 368 is configured to be controlled by a controller 212.

Figure 12:
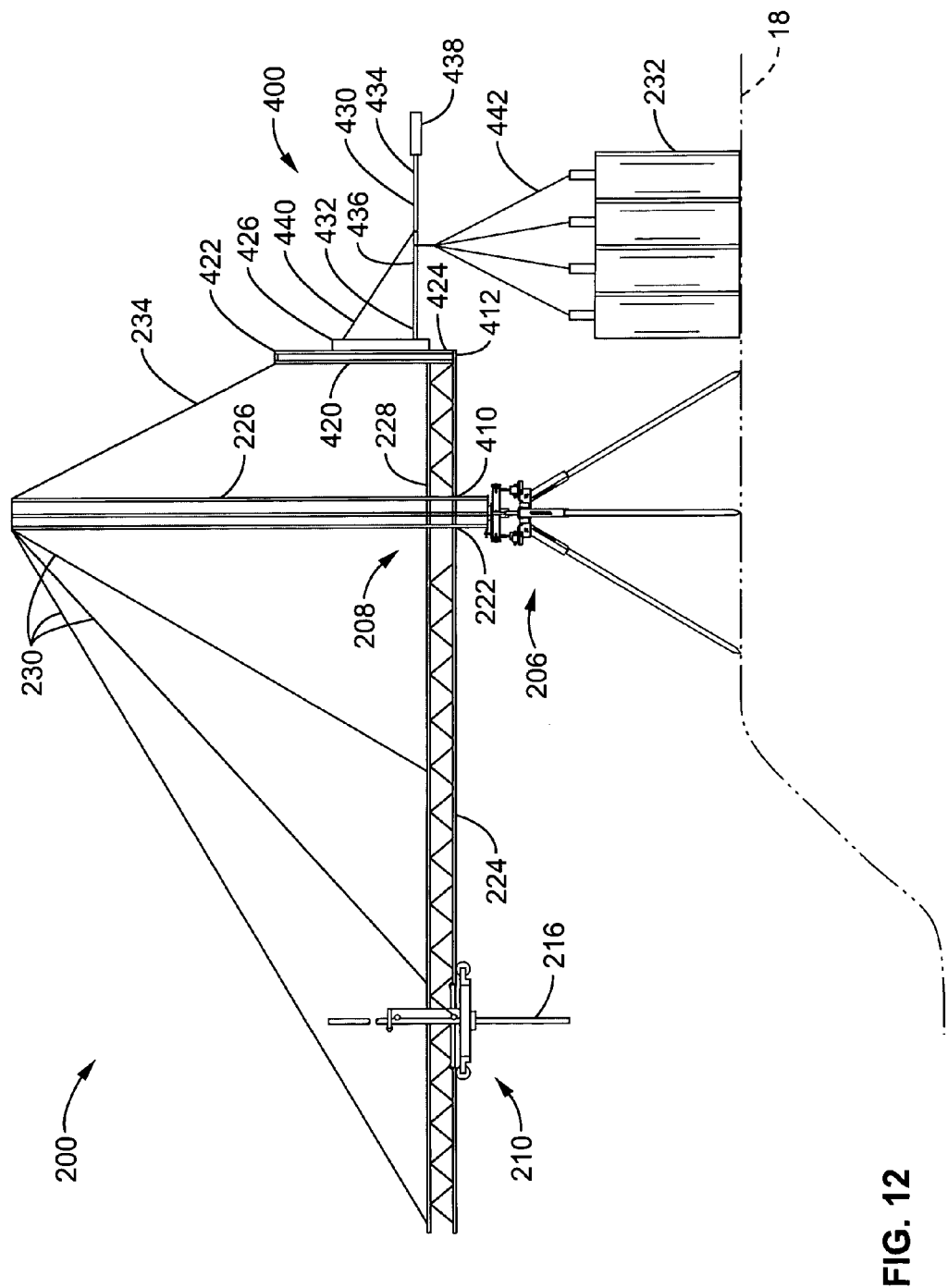
FIG. 12 illustrates an embodiment of a counterweight system for a portable robotic apparatus shown in FIG. 5.

FIG. 12 illustrates an embodiment of a counter weight adjustment system 400 as part of an automated portable apparatus 200, similar to the embodiment shown previously in FIG. 5. Apparatus 200 is positioned on ground 18 with platform 206 supporting boom structure 208 and automated carriage 210 supporting VMR 216 on swing boom 224. Counterweight boom 228 has a proximal end 410 and a distal end 412 with proximal end 410 coupled to the four way hub 222. Counterweight track 420 with a top end 422 and a lower end 424 is coupled vertically to distal end 412 of counterweight boom 228. One or more support wires 230 are connected from the swing boom 224, through the top of mast 226, and support wires 234 are connected from the top of mast 226 to the top end 422 of counterweight track 420. A counterweight carriage 426 is adapted to travel vertically on counterweight track 420 and has a securing device, such as a clamp (not shown), to hold counterweight carriage 426 at a desired elevation on counterweight track 420.

A support arm 430 has a proximal end 432, distal end 434 and a midportion 436. Support arm 430 is hingedly coupled to counterweight carriage 426 at proximal end 432 and projects horizontally in a direction opposite from swing boom 224. In one embodiment, support arm 430 is configured with a handle 438 at the distal end 434. In a further embodiment, a counterweight support cable 440 is coupled to counterweight carriage 426 and near mid portion 436 of support arm 430. Cables 442 are attached to one or more bags of water 232 (as shown previously in FIG. 5) and are configured to suspend bags of water 232 from support arm 430 at midportion 436. In operation, swing boom 224 is oriented for measurement on platform 206 as previously discussed. Counterweight carriage 426 is positioned on counterweight track 420 so the bags of water 232 are partially supported on the ground 18. When the automated carriage 210 moves outward on swing boom 224, the resulting increase in cantilever force can be offset by moving counterweight carriage 426 up on vertical counterweight track 420 and therefore raising the bags of water 232 so more water weight is supported by counterweight carriage 426. The bags of water 232 can be temporarily lifted off the ground 18 for reorienting swing boom 224 by lifting handle 438 on the support arm 430. In another embodiment, the length of the counterweight support cable 440 can be adjusted during operation, such as with a turnbuckle, to adjust the water weight supported on support arm 430 or reorient swing boom 224.

Figure 13:
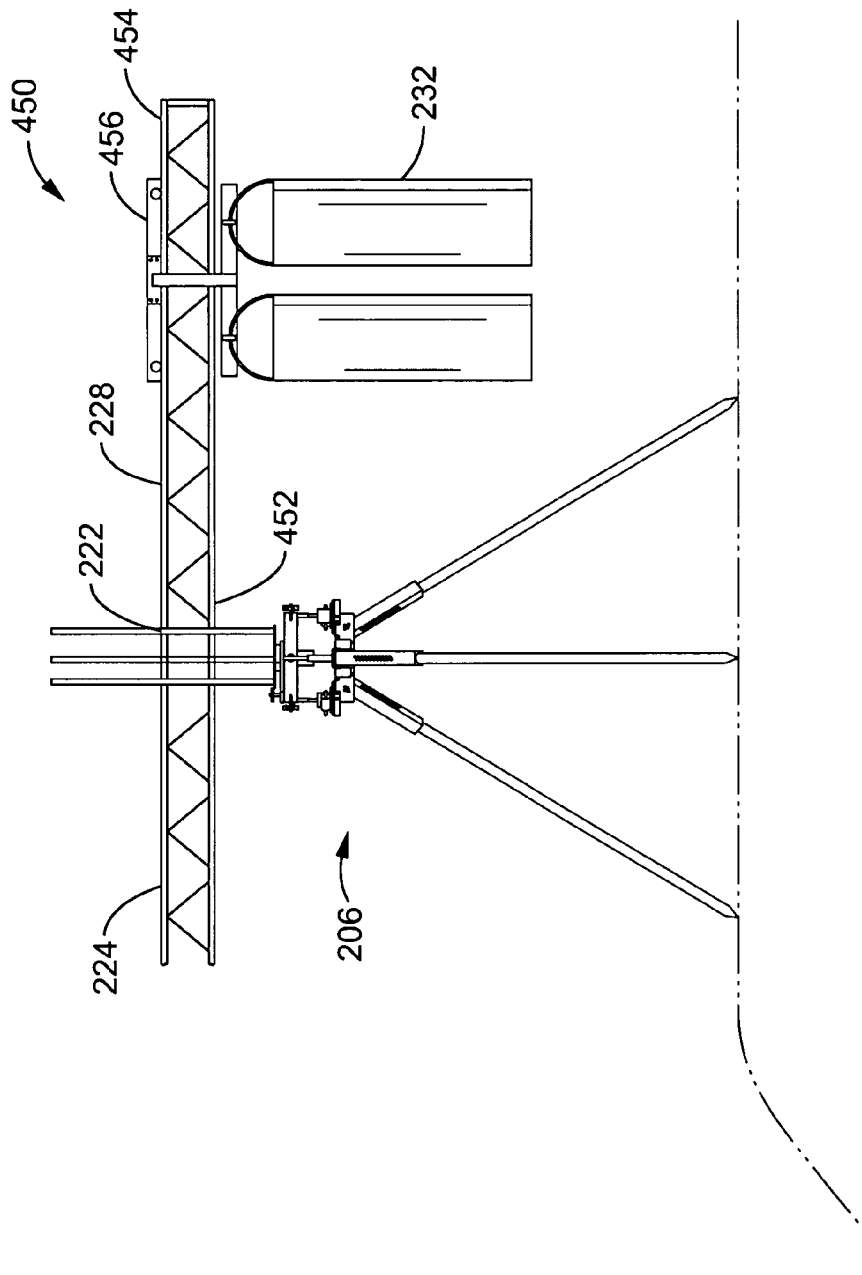
FIG. 13 illustrates another embodiment of a counterweight system for a portable robotic apparatus shown in FIG. 5.

FIG. 13 illustrates another embodiment of a counter weight adjustment system 450 for a portable robotic apparatus as shown previously in FIG. 12. A horizontal counterweight boom 228 has proximal end 452 and distal end 454. Counterweight boom 228 is coupled to the four way hub 222 at proximal end 452 and supported on leveling platform 206. A counterweight carriage 456 is configured to travel horizontally on counterweight boom 228 and support bags of water 232 or other heavy objects such as rocks. When automated carriage 216 repositions on swing boom 224 (as discussed previously in FIG. 12), the change in cantilever force is offset by moving counterweight carriage 456 in an opposite direction on counterweight boom 228. In a further embodiment (not shown), counterweight carriage 456 is provided with a motor drive and configured to reposition on counterweight boom 228 in response to; the change of position of automated carriage 210 on swing boom 224, signals from a level indicator, or signals from the operator through controller 212 (shown in FIG. 5).

Figure 14:
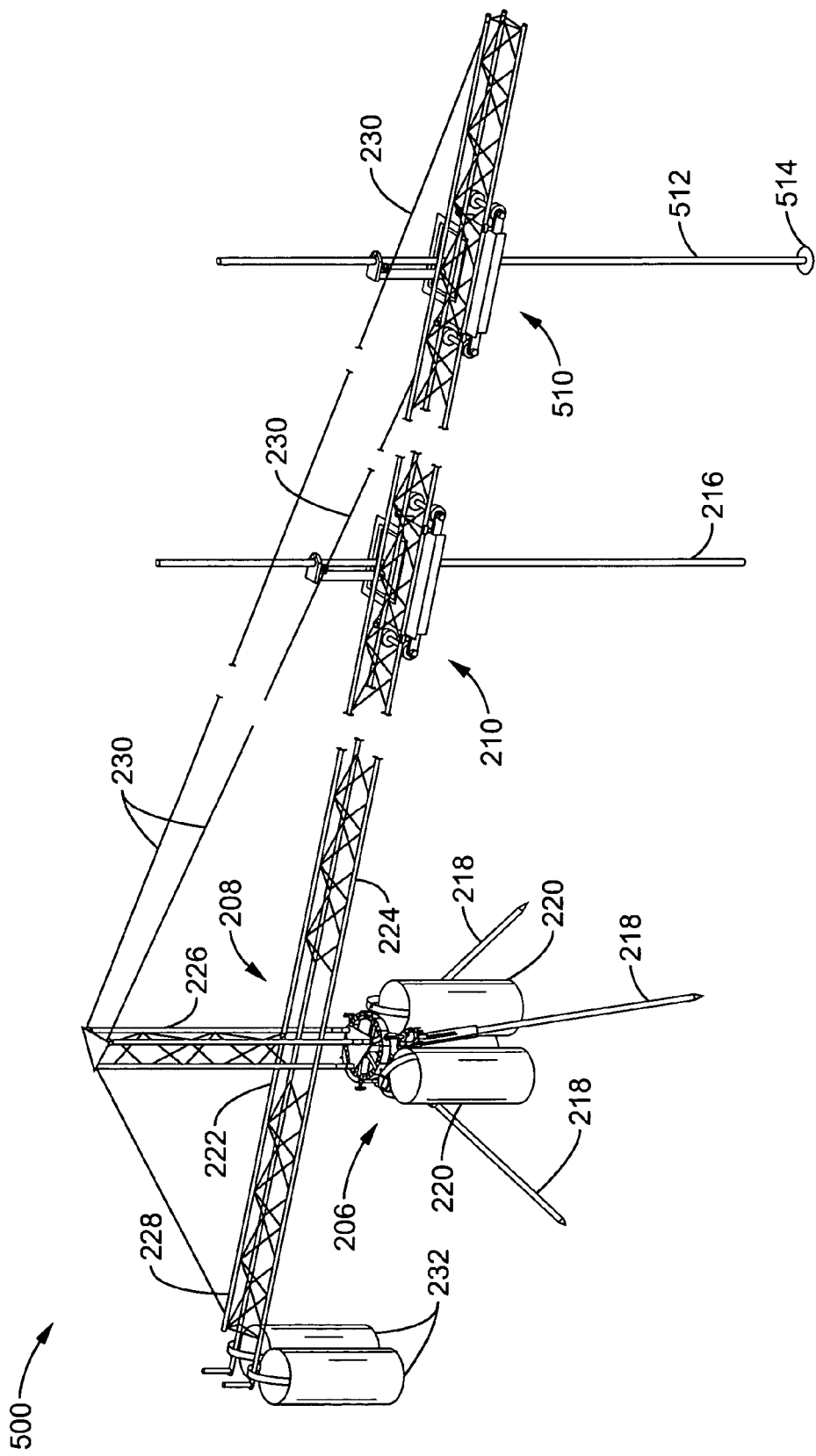
FIG. 14 illustrates a robotic apparatus as shown in FIG. 5 with a support carriage and support rod on the swing boom.

FIG. 14. illustrates another embodiment of a robotic portable apparatus for measuring a hydraulic feature, generally designated as 500. The apparatus is configured similar to the apparatus described in FIG. 5 with a support carriage assembly 510 added and positioned at the far end of swing boom 224. Support carriage assembly 510 is configured with a drive system similar to carriage assembly 210 described previously in FIG. 8 through FIG. 11 and is adapted to position a support rod 512 so that foot 514 of support rod 512 is positioned on the channel bottom to provide additional support to swing boom 224. Support foot 514 may be a horizontal planar shape for use in soft sand, sediment or mud. A gimbal system (as previously described in FIG. 8 through FIG. 11) on support carriage assembly 510 can be used to position support rod 512 in orientations other than vertical. In one embodiment, swing boom 224 can be extended to about 80 feet by utilizing a support carriage assembly 510. In another embodiment (not shown), a safety cable is coupled to the lower end of support rod 512 and through a pulley on support carriage assembly 510 (see FIG. 4) and used to raise support rod 512 and retrieve carriage 510 in the event of a power or equipment failure.

It is contemplated that another embodiment of support carriage assembly 510 and support rod 512 would have some or all of the manual positioning features of carriage 160 and measuring rod 180 as previously described in FIG. 4. Additionally, support rod 512 could be configured to accommodate sensors or sampling equipment as previously described in FIG. 4.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A portable apparatus for measuring characteristics of a hydraulic feature in a river or stream, comprising:
   a measuring rod, said measuring rod adapted to measure characteristics of a hydraulic feature;
   means for positioning said measuring rod in a desired location relative to a hydraulic feature, comprising:
     a boom, said boom oriented horizontally and coupled to said platform;
     said boom adapted to articulate on a vertical axis through said platform;
     said boom further adapted to extend over a hydraulic feature; and
     a carriage, said carriage adapted to travel along said boom;
     said carriage further adapted to position said measuring rod vertically;
     wherein said measuring rod is positioned to measure a characteristic of a hydraulic feature when said boom is positioned at a desired orientation on said platform, said carriage is positioned at a desired location on said boom, and said measuring rod is positioned at a desired elevation relative to a hydraulic feature;
   a support carriage, said support carriage adapted to travel on said boom;
     a support rod, said support rod slidingly coupled to said support carriage;
     said support rod adapted to contact the ground and provide vertical support to said boom through said support carriage;
     wherein said boom is supported when said support carriage is positioned in a desired location on said boom and said support rod is positioned to contact the ground and is secured to said support carriage; and
   a platform;
   said platform adapted to support said positioning means;
   said platform further adapted for positioning adjacent the hydraulic feature.

2. An apparatus as recited in claim 1, wherein said measuring rod has a hollow hexagonal cross section.

3. An apparatus as recited in claim 1, wherein said measuring rod has a round tubular cross section.

4. An apparatus as recited in claim 1, wherein said measuring rod has a visual index to measure the position of said measuring rod relative to said positioning means.

5. An apparatus as recited in claim 1 wherein said measuring rod is adapted to accommodate sensors selected from a group comprising a differential pressure sensor, a time domain reflectometer, a current meter, a propeller, an electromagnetic velocimeter, an acoustic Doppler velocimeter, a digital camera and a video camera.

6. An apparatus as recited in claim 1, wherein said platform comprises a tripod having adjustable legs.

7. An apparatus as recited in claim 1, wherein said platform comprises:
a tripod, said tripod having adjustable legs;
a mast, said mast coupled to said tripod; and
a support cable having a first end, a mid portion and a second end;
said first end of said support cable coupled to said boom;
said mid portion of said support cable slidingly coupled to said mast; and
said second end of said support cable adapted to be coupled to an anchoring object.

8. An apparatus as recited in claim 1, wherein said means for positioning further comprises:
a winch, said winch coupled to said boom;
a winch cable, said winch cable having a first end and a second end, said first end coupled to said winch; and
a pulley, said pulley coupled to said carriage;
said pulley adapted to support said winch cable;
said second end of said winch cable coupled to said measuring rod;
wherein said measuring rod is repositioned upward when said winch cable is retracted by said winch through said pulley.

9. An apparatus as recited in claim 1:
wherein said boom comprises a truss with at least two legs; and
wherein said carriage is configured to travel on two legs of said truss.

10. An apparatus as recited in claim 1, wherein said apparatus is adapted to measure characteristics selected a group comprising air quality and water quality, and characteristics pertaining to weather, soils, sediments, volcanic gases, and hydrothermal fluids.

11. An apparatus as recited in claim 10 wherein said apparatus is adapted to accommodate sensors selected from a group comprising a particle collector, an air sample collector, a diffusive sampler, a thermometer, a psychrometer, a solar radiation detector, a barometer, an air speed indicator, a Nansen-type bottle, an alpha sampler, a pressure-valve sampler, an automated ISCO-type pump sampler, a gravity sediment corer with a core-catcher, an Eckma n-type dredge, and an all-plastic Nansen-type bottle.

12. A portable apparatus for measuring characteristics of a hydraulic feature in a river or stream, comprising:
a platform, said platform adapted for positioning adjacent to a hydraulic feature;
a boom, said boom coupled to said platform;
said boom adapted to be oriented horizontally relative to said platform;
said boom adapted to articulate on a vertical axis through said platform;
said boom further adapted to extend over a hydraulic feature;
a carriage, said carriage adapted to travel along said boom;
means for positioning said carriage on said boom;
a measuring rod, said measuring rod slidingly coupled to said carriage;
said measuring rod having a measuring end, said measuring end adapted to measure a characteristic of a hydraulic feature; and
means for positioning said measuring rod vertically relative to said carriage;
wherein said measuring rod is positioned to measure a characteristic of a hydraulic feature when said boom is positioned at a desired orientation on said platform, said carriage is positioned at a desired location on said boom, and said measuring end of said measuring rod is positioned at a desired elevation relative to a hydraulic feature;
a support carriage, said support carriage adapted to travel on said boom; and
a support rod, said support rod slidincily coupled to said support carriage;
said support rod adapted to contact the ground and provide vertical support to said boom through said support carriage;
wherein said boom is supported when said support carriage is positioned in a desired location on said boom and said support rod is positioned to contact the ground and is secured to said support carriage.

13. An apparatus as recited in claim 12, wherein said platform comprises a tripod having adjustable legs.

14. An apparatus as recited in claim 13, wherein said platform further comprises:
a mast, said mast coupled to said platform; and
a support cable having a first end, a mid portion and a second end;
said first end of said support cable coupled to said boom;
said mid portion of said support cable slidingly coupled to said mast;
said second end of said support cable coupled to an anchoring object.

15. An apparatus as recited in claim 12, wherein said measuring rod has a hollow hexagonal cross section.

16. An apparatus as recited in claim 12, wherein said measuring rod has a round tubular cross section.

17. An apparatus as recited in claim 12, wherein said measuring rod has a visual index to measure the elevation of said measuring end of said measuring rod relative to said carriage.

18. An apparatus as recited in claim 12, wherein said means for positioning said measuring rod comprises:
a winch, said winch coupled to said boom;
a winch cable, said winch cable having a first end and a second end, said first end coupled to said winch; and
a pulley, said pulley coupled to said carriage;
said pulley adapted to support said winch cable;
said second end of said winch cable coupled to said measuring rod proximate said measuring end;
wherein said measuring end of said measuring rod is repositioned upward when said winch cable is retracted by said winch through said pulley.

19. An apparatus as recited in claim 12, wherein said measuring rod is adapted to accommodate sensors selected from a group comprising a differential pressure sensor, a time domain reflectometer, a current meter, a propeller, an electromagnetic velocimeter, an acoustic Doppler velocimeter, a digital camera and a video camera.

20. An apparatus as recited in claim 12, said means for positioning said carriage comprises:
  a positioning rod, said positioning rod coupled to said carriage;
  said positioning rod adapted to position said carriage at a desired location along said boom;
  said positioning rod configured to releasably couple to said platform when said carriage is positioned at a desired location on said boom.

21. An apparatus as recited in claim 12:
  wherein said boom comprises a truss with at least two legs; and
  wherein said carriage is adapted to travel on two legs of said truss.

22. An apparatus as recited in claim 12, wherein said apparatus is adapted to measure characteristics selected a group comprising air quality and water quality, and characteristics pertaining to weather, soils, sediments, volcanic gases, and hydrothermal fluids.

23. An apparatus as recited in claim 22, wherein said apparatus is adapted to accommodate sensors selected from the group consisting essentially of a particle collector, an air sample collector, a diffusive sampler, a thermometer, a psychrometer, a solar radiation detector, a barometer, an air speed indicator, a Nansen-type bottle, an alpha sampler, a pressure-valve sampler, an automated ISCO-type pump sampler, a gravity sediment corer with a core-catcher, an Eckman-type dredge, and an all-plastic Nansen-type bottle.

24. A portable apparatus for measuring characteristics of a hydraulic feature in a river or stream, comprising:
  a tripod, said tripod adapted for positioning adjacent to a hydraulic feature;
  a boom, said boom coupled to said tripod;
  said boom adapted to be oriented horizontally relative to said tripod;
  said boom adapted to articulate on a vertical axis through said tripod;
  said boom adapted to extend over a hydraulic feature;
  a support carriage, said support carriage adapted to travel on said boom;
  a support rod, said support rod slidingly coupled to said support carriage;
  said support rod adapted to contact the ground and provide vertical support to said boom through said support carriage;
  wherein said boom is supported when said support carriage is positioned in a desired location on said boom and said support rod is positioned to contact the ground and is secured to said support carriage;
  a mast, said mast coupled to said tripod;
  said mast oriented on a vertical axis through said tripod;
  a support cable having a first end, a mid portion and a second end;
  said first end of said support cable coupled to said boom;
  said mid portion of said support cable slidingly coupled to said mast;
  said second end of said support cable coupled to an anchoring object;
  a carriage, said carriage adapted to travel along said boom;
  a positioning rod, said positioning rod coupled to said carriage;
  said positioning rod adapted to position said carriage at a desired location along said boom;
  said positioning rod configured to releasably couple to said tripod; when said carriage is positioned at a desired location on said boom;
  a measuring rod, said measuring rod slidingly coupled to said carriage;
  said measuring rod oriented vertically;
  said measuring rod having a measuring end, said measuring end adapted to measure a characteristic of a hydraulic feature;
  a winch, said winch coupled to said boom;
  a winch cable, said winch cable having a first end and a second end, said first end coupled to said winch; and
  a pulley, said pulley coupled to said carriage;
  said pulley adapted to support said winch cable;
  said second end of said winch cable coupled to said measuring rod proximate said measuring end;
  wherein said measuring end of said measuring rod is repositioned upward when said winch cable is retracted by said winch through said pulley; and
  wherein said measuring rod is positioned to measure a characteristic of a hydraulic feature when said boom is positioned at a desired orientation on said tripod, said carriage is positioned at a desired location on said boom, and said measuring end of said measuring rod is positioned at a desired elevation relative to a hydraulic feature.

25. An apparatus as recited in claim 24, wherein said measuring rod is adapted to accommodate sensors selected from a group comprising a differential pressure sensor, a time domain reflectometer, a current meter, a propeller, an electromagnetic velocimeter, an acoustic Doppler velocimeter, a digital camera and a video camera.

26. An apparatus as recited in claim 24:
  wherein said boom comprises a truss with at least two legs; and
  wherein said carriage adapted to travel on two legs of said truss.

27. An apparatus as recited in claim 24, wherein said apparatus is adapted to measure characteristics selected a group comprising air quality and water quality, and characteristics pertaining to weather, soils, sediments, volcanic gases, and hydrothermal fluids.

28. An apparatus as recited in claim 27, wherein said apparatus is adapted to accommodate sensors selected from a group comprising a particle collector, an air sample collector, a diffusive sampler, a thermometer, a psychrometer, a solar radiation detector, a barometer, an air speed indicator, a Nansen-type bottle, an alpha sampler, a pressure-valve sampler, an automated ISCO-type pump sampler, a gravity sediment corer with a core-catcher, an Eckman-type dredge, and an all-plastic Nansen-type bottle.

29. A method of measuring characteristics of a hydraulic feature in a river or stream, comprising:
  providing a portable hydraulic feature measuring apparatus, said apparatus comprising a platform, a boom, a carriage and a measuring rod;
  positioning said platform adjacent a hydraulic feature;
  positioning said boom on said platform in a desired orientation;
  positioning said carriage on said boom in a desired location on said boom;
  providing a support carriage and a support rod;
  positioning said support carriage on said boom in a desired location on said boom;
  positioning said support rod to contact the ground;
  securing said support rod to said support carriage;
  positioning said measuring rod at a desired elevation; and
  measuring a characteristic of a hydraulic feature through said measuring rod.

* * * * *